US008381498B2

(12) United States Patent  
Epstein

(10) Patent No.: US 8,381,498 B2
(45) Date of Patent: Feb. 26, 2013

(54) METHOD OF MANUFACTURING A DRESSING PACKAGE

(76) Inventor: Marc Irwin Epstein, New York, NY (US)

(*) Notice: Subject to any disclaimer, the term of this patent is extended or adjusted under 35 U.S.C. 154(b) by 0 days.

(21) Appl. No.: 13/537,224

(22) Filed: Jun. 29, 2012

(65) Prior Publication Data

US 2013/0019569 A1     Jan. 24, 2013

Related U.S. Application Data

(60) Provisional application No. 61/572,747, filed on Jul. 20, 2011.

(51) Int. Cl.
*B65B 5/04* (2006.01)
*A61F 17/00* (2006.01)

(52) U.S. Cl. ............... 53/452; 53/450; 602/55; 602/58; 602/79

(58) Field of Classification Search ............... 53/452, 53/453, 461, 450; 602/55, 58, 79
See application file for complete search history.

(56) References Cited

U.S. PATENT DOCUMENTS

| | | | |
|---|---|---|---|
| 4,472,480 A | 9/1984 | Olson | |
| 4,513,739 A | 4/1985 | Johns | |
| 4,706,662 A | 11/1987 | Thompson | |
| 4,832,008 A | 5/1989 | Gilman | |
| 4,915,102 A * | 4/1990 | Kwiatek et al. | 604/307 |
| 4,915,228 A | 4/1990 | Johns | |
| 5,018,516 A | 5/1991 | Gilman | |
| 5,106,629 A | 4/1992 | Cartmell et al. | |
| 5,160,315 A | 11/1992 | Heinecke et al. | |
| 5,336,162 A | 8/1994 | Ota et al. | |
| 5,397,297 A | 3/1995 | Hunter | |
| 5,412,035 A | 5/1995 | Schmitt et al. | |
| 5,415,627 A | 5/1995 | Rasmussen et al. | |
| 5,423,737 A | 6/1995 | Cartmell et al. | |
| 5,511,689 A | 4/1996 | Frank | |
| 5,525,422 A * | 6/1996 | Spies et al. | 428/355 AC |
| 5,685,833 A | 11/1997 | Turngren | |
| 5,726,250 A | 3/1998 | Zajaczkowski | |
| 5,738,642 A | 4/1998 | Heinecke et al. | |
| 5,755,681 A | 5/1998 | Plews | |
| 5,951,505 A | 9/1999 | Gilman et al. | |
| 5,998,694 A | 12/1999 | Jensen et al. | |
| 6,008,429 A | 12/1999 | Ritger | |
| 6,124,522 A | 9/2000 | Schroeder | |
| 6,149,614 A | 11/2000 | Dunshee et al. | |
| 6,184,264 B1 | 2/2001 | Webster | |

(Continued)

FOREIGN PATENT DOCUMENTS

EP     0066899 B1     3/1988

OTHER PUBLICATIONS

AAO LLC, "Quik Strip—It's what sets us apart" (http://asomedical.com/products/skin1/pages/US/video_flash.html) Listed Copyright date 2007.

*Primary Examiner* — Hemant M Desai
*Assistant Examiner* — Gloria R Weeks
(74) *Attorney, Agent, or Firm* — Weitzman Law Offices, LLC

(57) ABSTRACT

A method of making a packaged dressing involves coating a pattern of detachable high tack pressure sensitive adhesive on a cover material such that the cover material includes a tackless area; forming a release island on a backing material; and sandwiching a dressing between the cover material and the backing material such that the adhesive on the dressing abuts the release island, and the pattern of adhesive on the cover material adheres to and supports the dressing along its extent except for the portion overlying the tackless area and hermetically seals the dressing within the package.

17 Claims, 14 Drawing Sheets

U.S. PATENT DOCUMENTS

| | | |
|---|---|---|
| 6,225,522 B1 | 5/2001 | Schroeder |
| 6,297,422 B1 | 10/2001 | Hansen et al. |
| 6,346,653 B1 * | 2/2002 | Sessions et al. ............... 602/42 |
| 6,350,339 B1 | 2/2002 | Sessions |
| 6,495,230 B1 | 12/2002 | do Canto |
| 6,573,421 B1 | 6/2003 | Lemaire |
| 6,706,940 B2 | 3/2004 | Worthley |
| 6,822,132 B2 | 11/2004 | Ahrens et al. |
| 6,838,589 B2 | 1/2005 | Liedtke et al. |
| 6,878,385 B2 | 4/2005 | Jensen et al. |
| 6,905,100 B2 | 6/2005 | Franck et al. |
| 6,921,844 B2 * | 7/2005 | Cantor ............................ 602/41 |
| 7,518,031 B2 | 4/2009 | Liedtke et al. |
| 7,521,586 B2 | 4/2009 | Schroeder |
| 7,797,802 B2 * | 9/2010 | Ackerman ..................... 24/416 |
| 7,858,838 B2 | 12/2010 | Holm et al. |
| 7,888,546 B2 * | 2/2011 | Marcoux et al. ............... 602/52 |
| 8,021,347 B2 | 9/2011 | Vitaris et al. |
| 8,084,665 B2 | 12/2011 | Liedtke et al. |
| 2008/0281246 A1 | 11/2008 | Effing et al. |
| 2009/0082710 A1 | 3/2009 | Vitaris |
| 2009/0118658 A1 * | 5/2009 | Tarinelli et al. ................. 604/1 |
| 2009/0187130 A1 | 7/2009 | Asmus et al. |
| 2010/0222731 A1 | 9/2010 | Gajiwala |
| 2011/0166492 A1 | 7/2011 | Holm et al. |
| 2011/0257574 A1 | 10/2011 | Svensby |

* cited by examiner

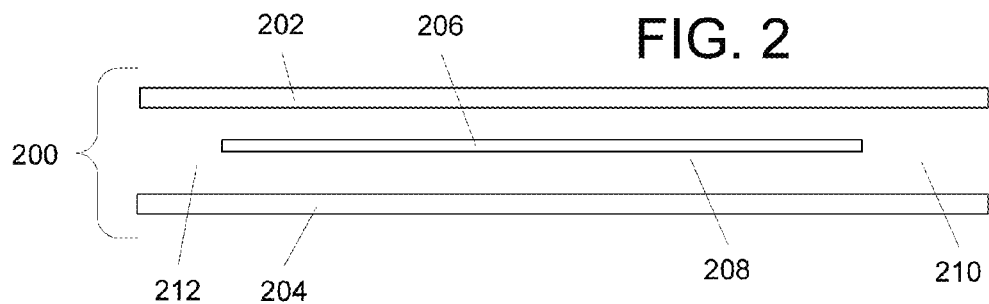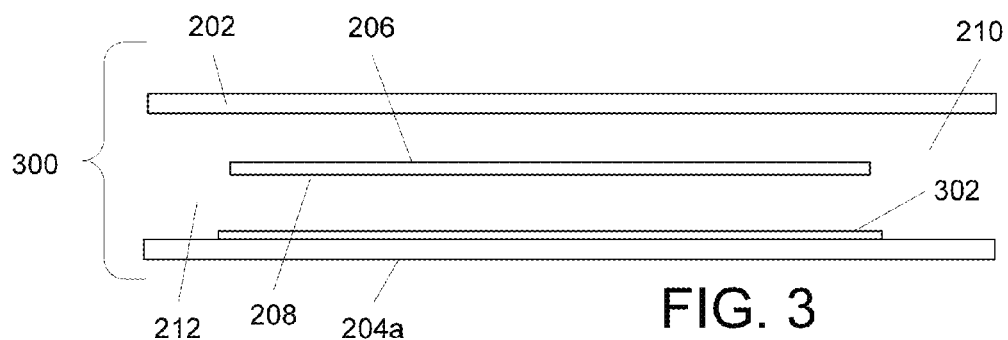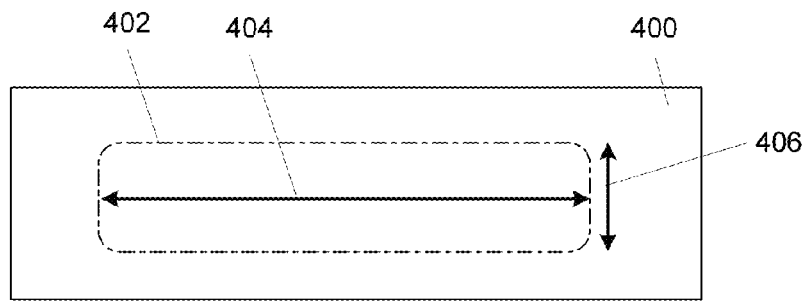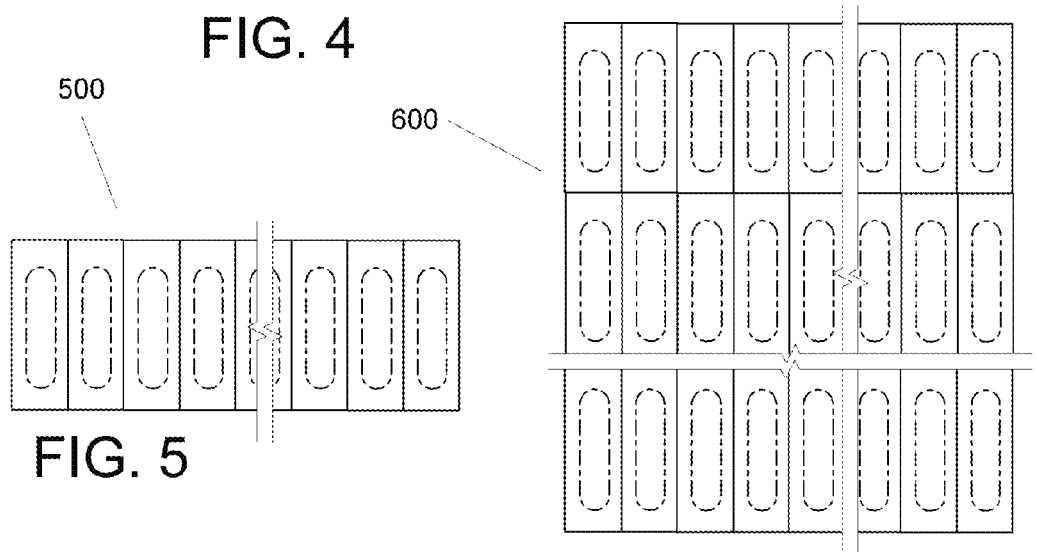

FIG. 11e
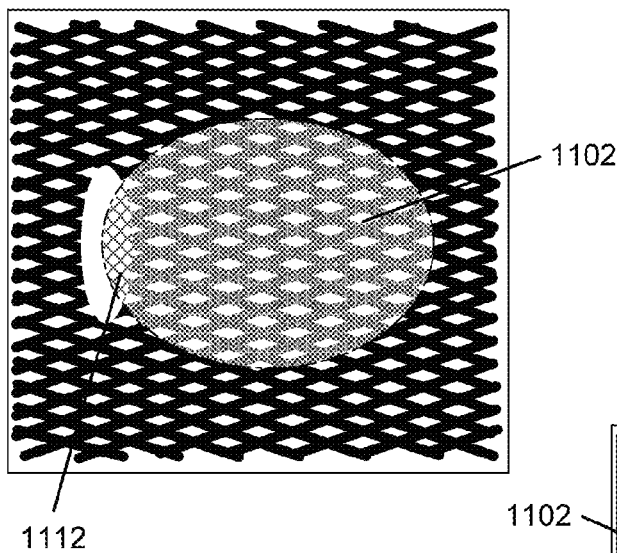
FIG. 11f
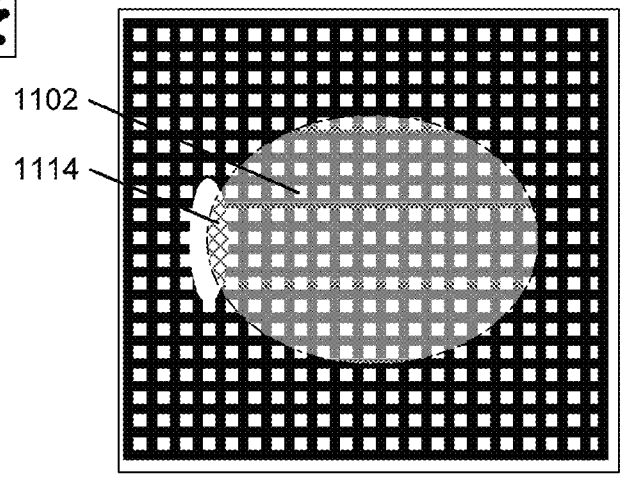
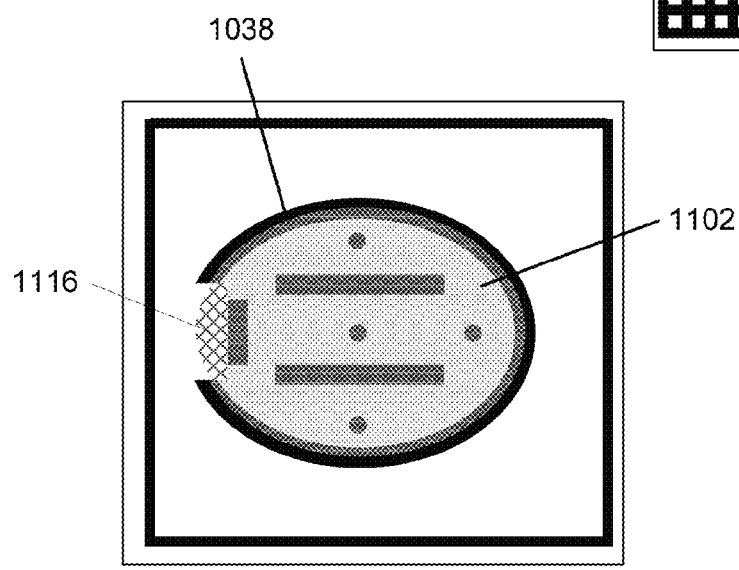
FIG. 11g

METHOD OF MANUFACTURING A DRESSING PACKAGE

CROSS REFERENCE TO RELATED APPLICATION

This application claims the priority benefit of U.S. Provisional Patent Application No. 61/572,747, filed Jul. 20, 2011, the disclosure of which is incorporated herein by reference in its entirety as if fully set forth herein.

BACKGROUND

1. Field

This disclosure relates generally to packaging, and, more particularly, to a method of packaging a dressing designed to be affixed to the skin, such as a dressing for a wound, a medicated patch or a nasal dilator strip.

2. Background

Dressings designed to be applied to the skin come in an almost limitless array of shapes and sizes. Moreover, such dressings are used in many different ways. Since, they are designed to be applied to the skin, it is important that they not harbor pathogens that could cause (or increase) any undesirable adverse effect or adversely affect the desired benefit they are intended to have, particularly in the case of medicinal dressings. Thus, common to all, is often the need to package them in a way that allows them to remain sterile until use is required and to allow them to be easily removed from the package and applied to the skin when use is required.

It has long been a known problem that, if a user of such a dressing has to touch the part of the dressing intended to be applied to the skin during application, it increases the risk of contamination of the dressing with undesired pathogens. In addition, many packages that are configured to address the above problem are either difficult to open and apply the dressing without undesirable touching and potential contamination of the dressing or are more costly to manufacture because they employ elaborate multi-piece configurations involving multiple steps.

Moreover, such dressings are sold by the millions on an annual basis. At the volumes manufactured and sold, even a slight cost increase in the manufacturing process (whether due to the need for additional materials and/or processing steps) can have a significant effect on profits.

Thus, there is still a need for a way to manufacture a package for a dressing that has a lower material and/or manufacturing processing cost and will still maintain a dressing in sterile condition until needed and, when use is required, be easy to use, and can help avoid undesirable touching and potential contamination of the dressing while it is affixed to the skin.

BRIEF SUMMARY

One aspect of the invention involves a method of making a packaged dressing for a dressing having a width, an extent and a perimeter. The dressing includes a skin adhering side having an affixation adhesive thereon, and a back side opposite the skin adhering side. The dressing further has a first terminus at one end of the extent and a second terminus at the other end of the extent, the second terminus defining an opening end for the packaged dressing. The method involves coating a first surface of a cover material with a detachable high tack, pressure sensitive adhesive in a predetermined pattern on the surface of the cover material such that (i) the first surface of the cover material includes at least one tackless area which is devoid of adhesive and disposed to correspond to and encompass at least a substantial portion of an edge of the first terminus and at least a portion of the surface of the cover material just beyond the edge of first terminus, (ii) the high tack, pressure sensitive adhesive forms at least a closed shape that encompasses within it both the tackless area and a dressing receiving area, and (iii) the high tack, pressure sensitive adhesive is disposed to affix the back side of the dressing to the first surface of the cover material along the extent of the dressing except for the tackless area when the back side of the dressing is brought into contact with the high tack, pressure sensitive adhesive on the first surface of the cover material.

The method also involves forming a release island on a first surface of a backing material, the release island having a size and shape corresponding to the width, extent and perimeter of the dressing.

The method further involves sandwiching the dressing between the first surface of the cover material and the first surface of the backing material such that (i) the skin adhering side of the dressing will be in contact with and substantially correspond to the release island, (ii) substantially all of the extent of the back side of the dressing will be in contact with, and held by, the high tack, pressure sensitive adhesive on the first surface of the cover material, (iii) a substantial portion of the edge of the first terminus of the back side of the dressing overlays the tackless area and defines an application end for the dressing, and (iv) the closed shape of high tack, pressure sensitive adhesive forms a hermetic seal about the dressing encompassing at least the entire perimeter of the dressing and the tackless area on the first surface of the cover material.

Another aspect of the invention involves a method of making a packaged dressing, the dressing having a width, an extent and a perimeter, the dressing comprising a skin adhering side having an affixation adhesive thereon, and a back side opposite the skin adhering side, the dressing further comprising a first terminus at one end of the extent and a second terminus at the other end of the extent, the second terminus defining an opening end for the packaged dressing. The method includes coating at least a portion of a first surface of a cover material with a detachable high tack, pressure sensitive adhesive. The method further includes modifying the tack of at least one predetermined area of the detachable high tack, pressure sensitive adhesive in a predetermined pattern so that the at least one predetermined area becomes a tackless area bounded by unmodified high tack, pressure sensitive adhesive, and such that, following the modifying, the high tack, the pressure sensitive adhesive that was not subject to the modifying will be unmodified high tack, pressure sensitive adhesive and will include a dressing receiving area, the predetermined area being located (i) so as to correspond to and encompass at least a substantial portion of an edge of the first terminus and at least a portion of the surface of the cover material just beyond the edge of the first terminus, (ii) such that the unmodified high tack, pressure sensitive adhesive will be disposed to affix the back side of the dressing to the first surface of the cover material along most of the extent of the dressing when the back side of the dressing is brought into contact with the unmodified high tack, pressure sensitive adhesive on the first surface of the cover material in the dressing receiving area.

The method also involves forming a release island, on a first surface of a backing material, having a size and shape corresponding to at least the width, extent and perimeter of the dressing.

The method additionally involves sandwiching the dressing between the first surface of the cover material and the first surface of the backing material such that (i) the skin adhering side of the dressing will be in contact with and substantially correspond to the release island, (ii) substantially all of the extent of the back side of the dressing will be in contact with, and held by, the unmodified high tack, pressure sensitive adhesive in the dressing receiving area on the first surface of the cover material, (iii) a substantial portion of the edge of the first terminus of the back side of the dressing overlays the tackless area, and (iv) the unmodified high tack, pressure sensitive adhesive will form a hermetic seal encompassing at least the entire perimeter of the dressing and the tackless area.

The foregoing has outlined rather generally the features and technical advantages of one or more embodiments of this disclosure in order that the following detailed description may be better understood. Additional features and advantages of this disclosure will be described hereinafter, which may form the subject of the claims of this application.

BRIEF DESCRIPTION OF THE DRAWINGS

This disclosure is further described in the detailed description that follows, with reference to the drawings wherein the same reference number in different figures represent the same thing, and in which:

FIG. 2 illustrates, in simplified form, an exploded view of the structural components of one example variant of a package 200 according to one variant of the present approach;

FIG. 3 illustrates, in simplified form, an exploded view of the structural components of an alternative example variant of a package FIG. 4 illustrates, in simplified form, a surface of an example cover material;

FIG. 5 illustrates, in simplified form, a cover material configuration such as shown in FIG. 4, usable for constructing a 1 by "n" array of individual packages;

FIG. 6 illustrates, in simplified form, a configuration such as shown in FIG. 4, usable for constructing an "n" by "m" array of individual packages;

FIGS. 11a through FIG. 11g illustrate, in simplified form, the example cover materials of FIGS. 10a through 10g with a representative oval dressing abutting the adhesive on the cover material;

DETAILED DESCRIPTION

In simplified overview, the package described herein is designed to be manufactured for use with any type of dressing described herein. In this regard, for purposes of understanding, FIG. 1 illustrates, in simplified form, different representative examples of some types of prior art dressings with which can be packaged according to the approach described herein.

Note that, as used herein, the term "dressing" is intended to mean and encompass any material of any length or width that includes an affixation adhesive located on one surface of the material and that is designed to be removably or releasably affixed to a person's skin by that adhesive for remedial or protective purposes. Examples of dressings package-able as described herein include, conventional bandages (such as shown, for example, in U.S. Pat. Nos. 1,612,267 and 2,823, 672, with or without a gauze or other protective pad), hydrocolloid external wound dressings (for example, dressings made from Avery MED5573H 10 mm hydrocolloid film or other of the numerous commercially available hydrocolloid dressings), transdermal medicated patches, wound closure strips (also referred to as "butterfly bandages") and nasal dilator strips, to name a few. Note that these representative examples are not exhaustive and are merely intended to illustrate some variants of those dressings for purposes of understanding the packaging approach herein. In addition, while certain shapes, sizes and types are presented in FIG. 1, it is to be understood that the packaging approach variants described herein can be used with any size and shape dressing, the particular size, shape, material or physical construction of the dressing being irrelevant or unimportant to understanding the present application or claims.

Figure 1:
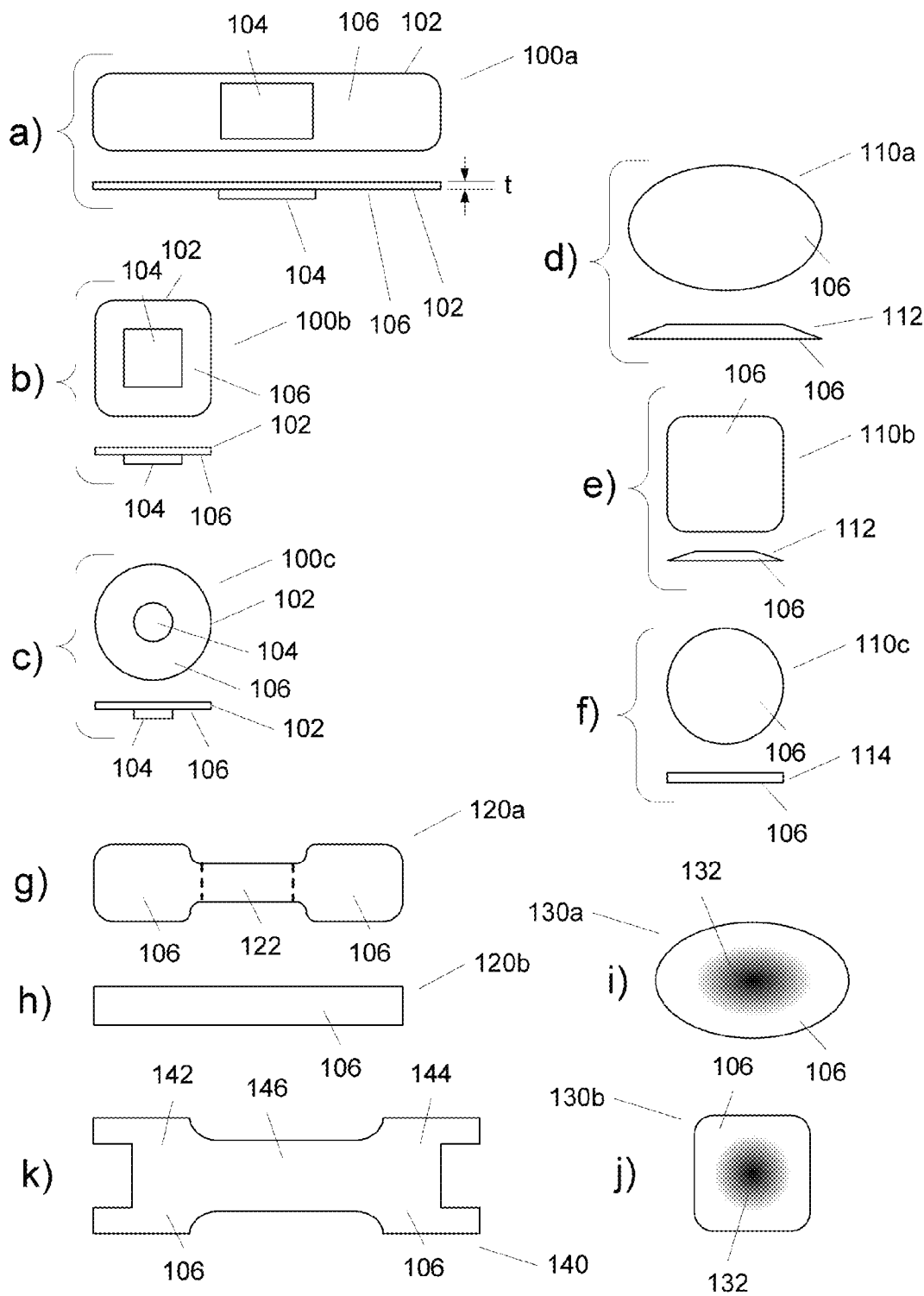
FIGS. 1a through 1k illustrate, in simplified form, different representative examples of some types of prior art dressings that can be packaged using the approach described herein.

Turning now to the specifics in FIG. 1, FIGS. 1a, 1b and 1c illustrate, in simplified fashion, some examples of more commonly recognizable wound dressings that can be packaged using the approach described herein. Specifically, FIGS. 1a, 1b and 1c illustrate some examples of conventional bandages, such as sold by Johnson & Johnson under the Band-Aid brand in both facing (i.e. skin adhering surface side) and side view.

The dressing 100a of FIG. 1a is made up of a bandage attachment material 102 of a thickness "t", an (optional) pad 104 which is generally sized and shaped for wound coverage, and an affixation adhesive 106 on at least a portion of the skin-side surface of the dressing which adheres the pad 104 to the attachment material 102 and in use, when applied, is intended to affix the dressing to skin. Depending upon the particular dressing, the thickness "t" of the attachment material 102 can be quite thin and the attachment material 102 itself can be exceedingly limp, loose, floppy or flexible.

FIG. 1b illustrates a wound dressing 100b configured in a "patch" shape, meaning that it is essentially square or slightly rectangular in shape, but otherwise is similar to the wound dressing of FIG. 1a.

FIG. 1c illustrates a wound dressing 100c configured in "spot" shape, i.e., it is essentially circular or slightly oval in shape, but is otherwise similar to the wound dressing of FIG. 1a.

FIGS. 1d, 1e and 1f illustrate, in simplified fashion, some examples of known dressings of the hydrocolloid type 110a, 110b, 110c. The different shapes shown are intended to illustrate that all shapes of these types of dressings can also be packaged according to the approaches described herein. As shown in FIGS. 1d, 1e and 1f, these dressings also have an affixation adhesive 106 on at least a portion of the skin-side surface of the dressing and, in some cases, the dressings can have a tapering reduction in thickness 112 closer to the perimeter edge (110a, 110b) or can be of relatively uniform thickness 114 about the perimeter edge.

FIGS. 1g and 1h illustrate, in simplified fashion, some examples of another known type of wound closure dressings 120a, 120b. These types of dressings 120a, 120b are designed to act like sutures and span a cut-type wound to hold both sides of the cut together. FIG. 1g illustrates a "butterfly" style wound closure 120a and FIG. 1h illustrates a "strip" style wound closure 120b. Again, as above, these different dressings are shown to illustrate that all shapes of these types of dressings can also be packaged according to the approaches described herein. As with the above these dressings 120a, 120b have an affixation adhesive 106 on at least a portion of the skin-side surface of the dressing, but may or may not specifically have affixation adhesive 106 in the region 122 that will be directly over the wound (shown in FIG. 1g as the region between the two dashed lines).

FIGS. 1i and 1j illustrate, in simplified fashion, some examples of known dressings of the transdermal patch type 130a, 130b. As above, these different shapes are intended to illustrate that all shapes of these type dressings can also be packaged according to the approaches described herein. As shown in FIGS. 1i and 1j, these dressings similarly have an affixation adhesive 106 on at least a portion of the skin-side surface of the dressing. In addition, such dressings typically are either impregnated with, or include a reservoir containing, the formulation 132 to be delivered transdermally via some or all of the skin-side surface of the dressing 130a, 130b following application to the skin.

It should be further understood that these packaging approaches are not limited to use with dressings associated with wounds or drug delivery. In this regard, FIG. 1k illustrates, in simplified form, a different type of dressing that can be packaged according to the approaches described herein. As shown, the dressing 140 of FIG. 1k is a nasal dilator strip type dressing. Nasal dilator strips typically includes affixation adhesive 106 at least near each end 142, 144 and may, or may not include adhesive near the central section 146. The adhesive is used to affix one end 142 of the dressing 140 to the skin on one side of the nose covering the alar fibrofatty tissue on that side of the nose and the other end 144 of the dressing 140 to the other side of the nose on the skin covering that side's alar fibrofatty tissue. The dressing 140 further includes a spring material designed to, when the dressing 140 is affixed to the nose, exert a force that drives the two ends 142, 144 away from each other and towards a flat configuration, thereby helping to keep the nostrils in an open position.

From the above, it should now be understood that the packaging approach described herein can be used with any type of removable dressing intended for application to the skin that includes adhesive on the skin contact side and, for which it is desirable to maintain the dressing in a sterile state while packaged.

Advantageously, the packaging approach variants described herein use fewer overall components and, thus, are simpler, than such other approaches.

By way of example, FIG. 2 illustrates, in simplified form, an exploded view of the structural components of one example variant of a package 200 according to one variant of the present approach. The package is made up of a cover material 202, a backing material 204, and a dressing 206 sandwiched between the cover material 202 and backing material 204 (with the adhesive side 208, i.e. skin affixation side, of the dressing 206 facing a release island area on the backing material 204) such that the dressing 206 will be hermetically sealed between the two by a high tack, pressure sensitive adhesive (not shown) the details of which are described in greater detail below. Thus, unlike other packages, the variants described herein provide a potentially significant cost savings by eliminating some of the materials typically used in other packages and, consequently, can reduce the number of steps involved in creation of the package, providing further savings thereby. One end 210 of the package is designated the "opening end" and that end 210 is the end by which the package will be opened. As will further be described below, through the processing described herein, the opposite end 212 of the package will be specifically configured to facilitate application of the dressing after opening.

FIG. 3 illustrates, in simplified form, an exploded view of the structural components of an alternative example variant of a package 300 that is similar to the variant of FIG. 2, except it includes one additional component. Specifically, this package 300 variant is made up of a cover material 202, a backing material 204a, a dressing 206, and a release island component 302 that is a different material from, and physically bonded to, the backing material 204a in any appropriate manner. Numerous suitable methods of bonding a release island component 302 to a substrate are well known in the dressing packaging art, and the particular method used is unimportant to understanding the instant invention. Thus, for simplicity and brevity, those methods are not described herein.

With the variant of FIG. 3, the dressing 206 is sandwiched between the cover material 202 and the release island component 302 bonded to the backing material 204a such that the dressing 206 will similarly be hermetically sealed between the cover material 202 and backing material 204, as in FIG. 2, by a high tack, pressure sensitive adhesive (not shown) but with the adhesive side (i.e. skin affixation side) 208 of the dressing 206 abutting the release island component 302 on the backing material 204a as opposed to a release island area of the backing material 204 of FIG. 2.

Although the structure of FIG. 3 uses one additional component, the release island component 302, and requires at least one additional step to bond the release island component 302 to the backing material 204a, a savings can still result relative to other packaging approaches as should be evident from the rest of the description.

Moreover, as is to be understood from the following description, additional benefits and advantages to the user flow from the instant packaging approach, which could lead to users prefer a package created according to one of the variants described herein over other available packages, resulting in increased sales volumes.

To further understand the packaging approach, some terminology as used herein and general configuration information will now be discussed with reference to FIGS. 4 through 21.

FIG. 4 illustrates, in simplified form, the surface of an example cover material 400 that will face the backside of an example dressing (the perimeter 402 of which is represented in this figure by a line of alternating dots and dashes) as described herein for one variant package. The shape of the cover material 400 and dressing placement location are pre-selected for manufacture so that the cover material 400 exceeds both the extent 404 and width 406 of the dressing with which it will be used by an amount sufficient to allow adhesive to encompass the entire perimeter 402 of the pertinent dressing as will be described.

It is to be further understood that, depending upon the particular implementation involved, the variants described herein can be created on a single unit basis such as shown in FIG. 4, or, as is more likely for mass production, on a multi-unit basis. For example, FIG. 5 illustrates, in simplified form, a cover material configuration such as shown in FIG. 4, usable for constructing a 1 by "n" array 500 of individual packages, where "n" is any desired number. Similarly, FIG. 6 illustrates, in simplified form, a configuration such as shown in FIG. 4, usable for constructing an "n" by "m" array 600 of individual packages, where "n" and "m" are any numbers, and may or may not be equal to each other (i.e. the array of FIG. 6 could be a square array where "n"="m" or a rectangular array where "n" "m").

Figure 7:
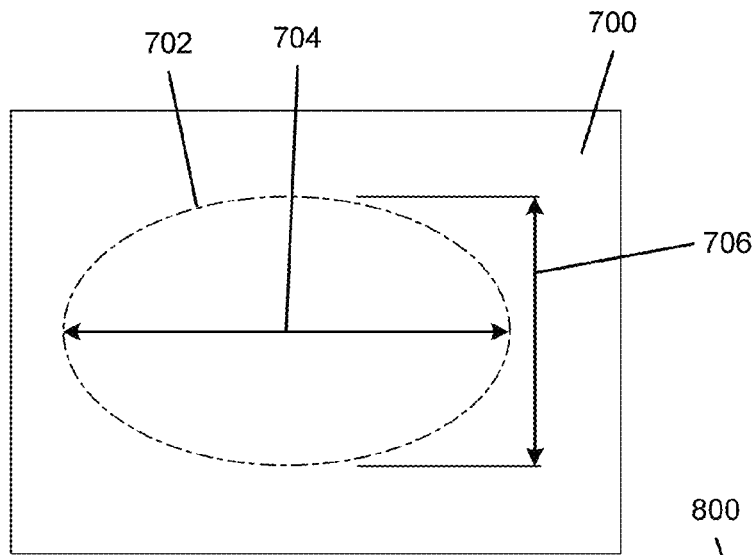
FIG. 7 illustrates in simplified form an alternative example of a rectangular cover material.

Moreover, the shape of the cover need not substantially correspond to the shape of the dressing with which it will be part of a package. FIG. 7 illustrates in simplified form an alternative example of a rectangular cover material 700 surface on the side that will face the backside of an example oval shaped dressing as described herein (the perimeter 702 of which is again represented by a line of alternating dots and dashes). Again, the dressing placement location relative to the cover material 700 is pre-selected for manufacture so that the cover material 700 exceeds both the extent 704 and width 706 of the dressing with which it will be used by an amount sufficient to encompass the entire perimeter 702 of the pertinent dressing.

Figure 8:
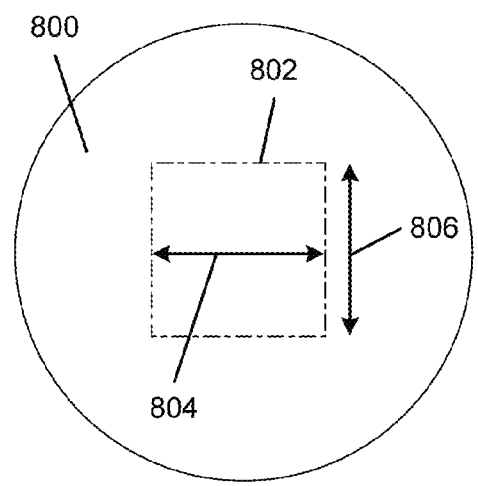
FIG. 8 illustrates, in simplified form, an alternative example of a circular cover material.

FIG. 8 illustrates, in simplified form, an alternative example of a circular cover material 800 surface on the side that will face the backside of an example square shaped dressing as described herein (the perimeter 802 of which is again represented by a line of alternating dots and dashes), for example to allow multiple such packages to be stored or dispensed from a cylindrical tube. Yet, again, the dressing placement location relative to the cover material 800 is pre-selected for manufacture so that the cover material 800 exceeds both the extent 804 and width 806 of the dressing by an amount sufficient to encompass the entire perimeter 802 of the pertinent dressing.

Figure 9:
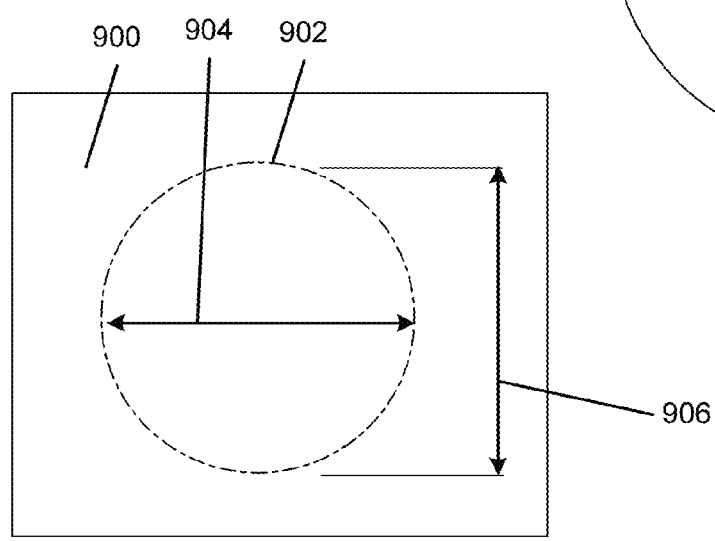
FIG. 9 illustrates, in simplified form, one more alternative example of a cover material.

FIG. 9 illustrates, in simplified form, one more alternative example of a cover material 900 showing the surface on the side that will face the backside of an example circular dressing as described herein, the perimeter 902 (i.e. circumference) of which is again represented by a line of alternating dots and dashes. Note that, for circular dressings, the extent 904 and width 806 are both equal and equate to the diameter of the dressing. For purposes of explanation, irrespective of the type of dressing, as a convention, the term "extent" will be used herein to refer to a direction along the (intended) package opening direction and the "width" will be used to refer to a direction substantially perpendicular to the extent.

Thus, it should now be understood that any combination of cover material shape and dressing shape can be used together provided the two are properly sized and positioned consistent with the description herein, and that different arrays and combinational approaches can be employed for purposes of manufacture.

With the above in mind, different variants of the packaging approach will now be described with reference to the remaining figures. Note that this aspect of the process presumes that a suitable cover material and backing material have already each been selected and, if multiple cover material and/or backing material components are to be created concurrently or sequentially (or some combination thereof), the unprocessed cover and/or backing material will be appropriately arrayed and situated for the steps that follow. Similarly, a detachable high tack, pressure sensitive adhesive (PSA) compatible with the cover material and backing material (for bonding them to each other as part of the process) will also have been selected. Moreover, the detachable high tack, PSA will have been selected from among those suitable for removably bonding the selected cover material to the selected backing material when they are brought together to seal the package. Note here that when referring to an adhesive used in creating the package, the term "detachable" is intended to mean a removable PSA that can withstand the rigors of service without unintentional detachment, can be purposefully detached without the need to re-attach (and may, or may not even be able to thereafter be re-attached). Moreover, even if reattachment is possible it will not hold with the same force, nor will it withstand the rigors of service in the same manner as the initial attachment, and it can suffer from unintentional detachment thereafter.

Now the cover material-related sub process will be discussed.

The cover material is arranged within conventional machinery capable of applying, and configured to apply, a predetermined pattern of the detachable high tack PSA onto the cover material. Note that the term "pattern" is used because, not only does the entire surface of the cover material not need to be covered, having areas either (i) without adhesive or (ii) where parts of the adhesive has had its tackiness rendered ineffective so that the remaining tacky adhesive forms a pattern, is an intentional and mandatory part of the process.

Depending upon the particular implementation of the process, the dressing, and the adhesive-applying machinery, the predetermined pattern can be any pattern provided that it meets at least two essential criteria. First, the pattern must be such that, when the final package is constructed, part of the pattern of detachable high tack PSA will form a closed shape that encompasses within it the entirety of the dressing to allow for formation of a hermetic seal about the dressing. Second, the pattern of the detachable high tack PSA must be arranged such that it will substantially affix the back side of the dressing to the cover across its width and along its extent, with the exception of a specific area to be described in greater detail below. The purpose of this is to ensure that substantially all of the extent of the dressing will be affixed to, and supported by, the cover when the backing is removed as part of the application process. The pattern can be applied using any machinery capable of applying a pattern of adhesive in this manner, however, it is believed that pattern printing of the adhesive provides advantages over other approaches in terms of, for example, cost and speed. A representative supplier who can perform pattern coating or pattern printing of adhesives in the manner described herein is Rayven Inc., of 431 Griggs Street N., St. Paul, Minn. 55104.

FIGS. 10a through 10g illustrate, in simplified form, some representative, non-exhaustive, non-limiting, examples of cover materials onto which patterns (representing some of the limitless patterns that could be used to fulfill the above criteria) have been applied. Note that, each also includes a specific area that, depending upon the particular variant, either (i) is devoid of adhesive or (ii) has been detackified/deactivated. these will described in greater detail below. An area which is either devoid of adhesive or has been detackified/deactivated will be referred to as a "tackless area" hereafter.

Figure 10A:
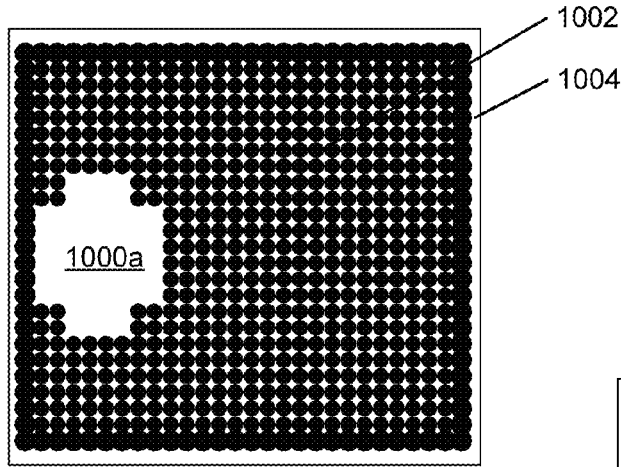
FIGS. 10a through 10g illustrate, in simplified form, some representative, non-exhaustive, non-limiting, examples of cover materials onto which patterns have been applied.
Figure 10B:
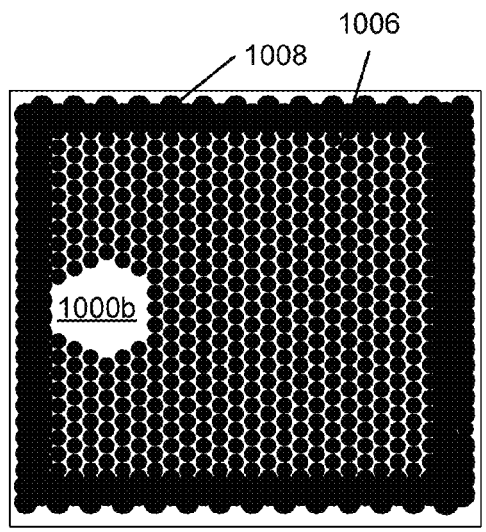
Figure 10C:
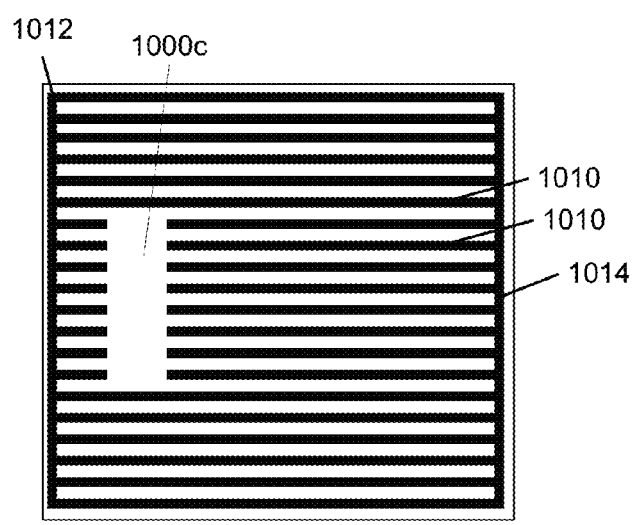
Figure 10D:
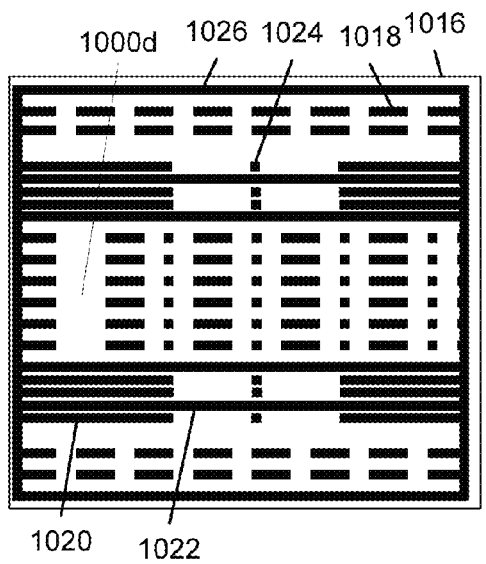
Figure 10E:
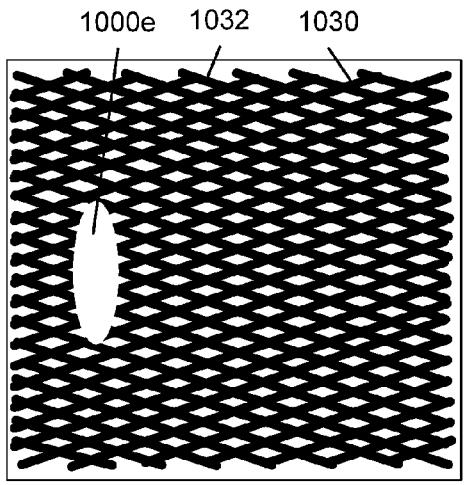
Figure 10F:
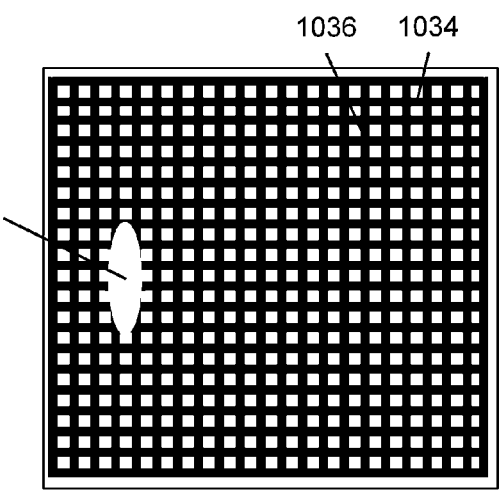
Figure 10G:
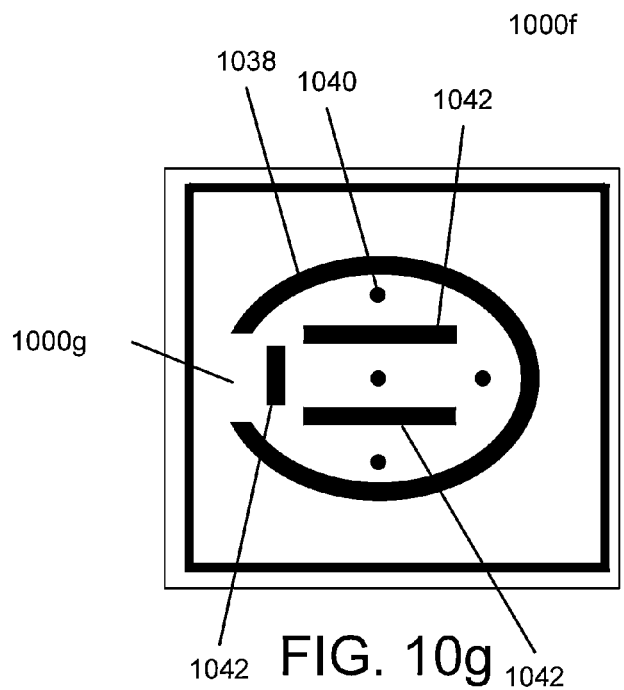
Figure 11A:
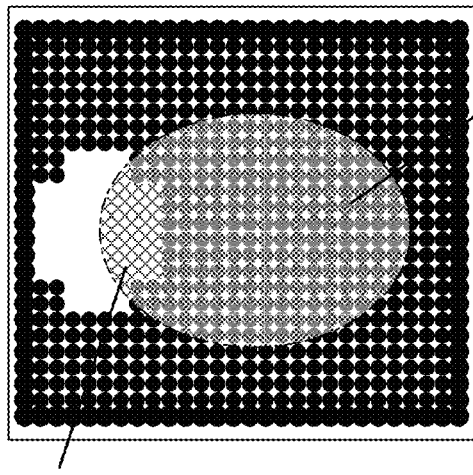
Figure 11B:
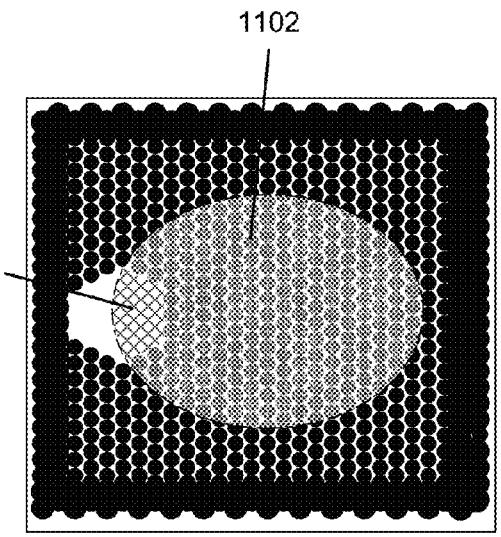
Figure 11C:
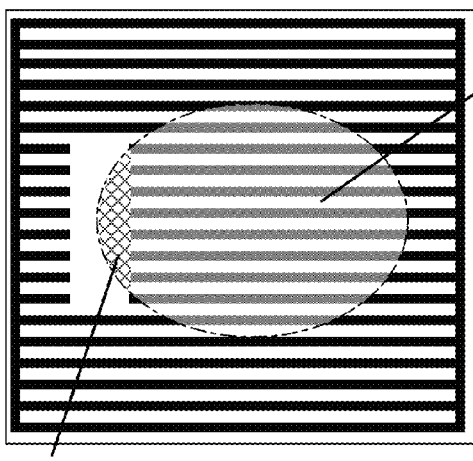
Figure 11D:
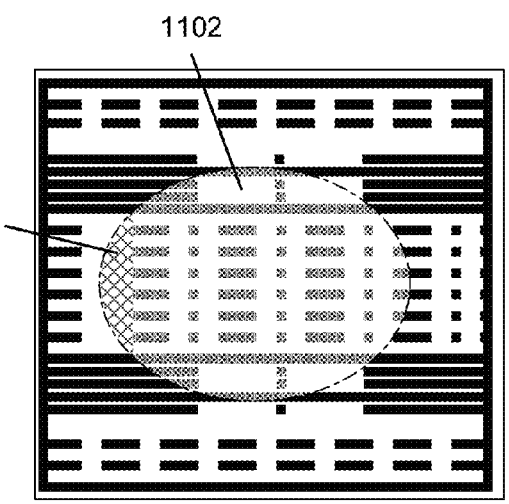

Specifically, FIG. 10a illustrates a cover material substantially covered with a pattern of evenly spaced apart, linearly-aligned dots of adhesive 1002. Those dots of adhesive 1002 are peripherally bounded at their extreme edge by a pattern of slightly larger, partially overlapping dots 1004. These overlapping dots 1004 form the closed shape used to form a hermetic seal about a dressing. There is also a tackless area 1000a bounded by the dots of adhesive 1002, 1004, near an edge that will be at the end opposite from the end from which the package will be opened. FIG. 10b illustrates a cover material with a pattern of evenly spaced apart, offset rows of dots of adhesive 1006, again bounded at the extreme edge by a pattern of slightly larger, partially overlapping dots 1008 and containing an elongated hexagon or truncated lozenge shaped tackless area 1000b near an edge that will be at the end opposite from the end form which the package will be opened. FIG. 10c illustrates a cover material with a pattern of evenly spaced apart lines of adhesive 1010, the outermost ends of which are connected to each other by a pair of lines of adhesive 1012, 1014 running perpendicular to those lines 1010. A substantially rectangular-shaped tackless area 1000c is present near an edge that will be at the end opposite from the end from which the package will be opened. FIG. 10d illustrates a cover material with a mixed pattern 1016 of adhesive made up of different length parallel lines 1018, 1020, 1022 of differing spacing, interspersed with dots 1024 of adhesive, with its overall perimeter bounded by a rectangle 1026 of adhesive for hermetic sealing. As with the prior figure example, the cover material of FIG. 10d also includes a substantially rectangular tackless area 100d. FIG. 10e illustrates a cover material with a pattern of intersecting lines 1030, 1032 of adhesive, with the lines having varying spacing between them along their length. In addition, FIG. 10e also includes a substantially oval shaped tackless area 1000e. FIG. 10f illustrates a cover material with a "cross hatch" pattern of perpendicularly intersecting lines 1034, 1036 of adhesive. FIG. 10g illustrates a cover material with a pattern made up of part of an example pattern of irregular shapes, in this case an oval arc 1038 of adhesive as well as some dots 1040 and differently oriented lines 1042, 1044 of adhesive.

As will now be seen, the placement of the tackless area relative to where the dressing will be is pre-specified in order to ensure a specific interaction between the cover and dressing. However, in general overview, a tackless area will at least be located near where the terminus of the dressing that will be farthest from the end of the package from which the package will be opened and partially underlie, and partially extend beyond, that terminus. Note here that the tackless area is said to "underlie" the dressing because it is between the back (i.e. non-skin facing side) side of the dressing and the adhesive side of the cover material, irrespective of the orientation of the cover material in space. Thus, in the same vein, part of the dressing will "overlay" the tackless area irrespective of the orientation of the cover material in space.

Specifically. to illustrate one set of examples as to how the packaging approach causes specific interaction between cover materials and dressings, FIG. 11a through FIG. 11g each illustrate, in simplified form, the representative, non-exhaustive, non-limiting, example cover materials of FIG. 10a through 10g with the back (i.e. non-skin facing side) side of a representative oval dressing 1102 (shown in peripheral outline only) abutting the adhesive on the cover material in the manner it would in the final formed package (and for the time between opening of the package and application of the dressing to the skin). As can be seen in each of FIGS. 11a through 11g, notwithstanding the areas where the dots and/or lines of adhesive have been applied, the dressing 1102 will be adhered to, and supported by, the cover material via that adhesive along its extent and width, less the specific portions of the dressing 1104, 1106, 1108, 1110, 1112, 1114, 1116 (in FIG. 1la indicated by cross hatching) that overlie the respective tackless areas. In addition, note that the tackless area of each is placed such that it also has a portion extending beyond the end periphery of the terminus of the dressing 1102. Advantageously, as can be seen, the fact that a pattern of adhesive was applied, instead of coating the entire surface of the cover material, allows for the saving of adhesive while still providing the requisite adherence and support along the extent of the dressing. Note further that, in FIG. 11g, the oval arc 1038 of adhesive is of sufficient width such that it both underlies the perimeter of the dressing 1102 (shown as partially transparent), other than in the tackless area, so as to adhere the dressing perimeter to the cover material and also extends beyond the outer perimeter of the dressing so that it will adhere the cover material to the backing material during package assembly.

FIGS. 12a through 12f, are similar to FIGS. 11a through 11f, except that FIGS. 12a through 12f illustrate portions of the cover materials of FIG. 11 and the outline of a rectangular dressing 1202. As can be seen if FIGS. 12a through 12f, by virtue of the adhesive pattern, the rectangular dressing will similarly be adhered to, and supported by, the cover material along its extent except for the portion 1204, 1206, 1208, 1210, 1212, 1214 (again shown by cross-hatching) where the tackless area underlies the dressing 1202 and extends slightly beyond its terminus 1216.

With the above in mind, it should now be noted that the tackless area can be formed differently, depending upon the particular process variant used to create the package. Specifically, it can be created as part of the adhesive application process itself or as part of a secondary sub-process following the adhesive application process.

For example, if the adhesive is applied using a pattern printing process, the tackless area can be integrated with and part of the predetermined pattern by allocating it as an area of the required size and shape where adhesive will not be applied. Alternatively, creation of the tackless area can occur after the adhesive pattern is applied by deactivating or detackifying some part(s) of the pattern of applied adhesive with a subsequent sub-step. To do so, the high tack PSA would be selected to be of a type and composition such that that is capable of being selectively deactivated or detackified in the intended area without affecting the tackiness in other areas where continuing tackiness is desired. Example, non-exhaustive, representative known methods for deactivating or detackifying PSA's include: UV curing, application of heat or cold, use of a dispersible adhesive material removable by selective exposure to a solvent or washing away of a tackifier or plasticizer, for example, as described in U.S. Pat. No. 5,726,250, cooling a PSA composition to below its melting point (for example, as in U.S. Pat. No. 5,412,035), exposing a light curing PSA composition with a photoinitiator to light, whether UV or some other wavelength in the visible or non-visible spectrum (for example, as in U.S. Pat. No. 6,184,264), or some other approach appropriate to the particular adhesive, the particular approach used for selectively detackifying or deactivating some of the adhesive being unimportant to understanding the process described herein. The foregoing patents are incorporated herein by reference in their entirety.

A related approach to selectively detackifying the high tack PSA would be to use a pattern printing process with a material that is itself (or can become) non-tacky and will be applied as an overcoat to cover or bind to the PSA where applied or to substantially eliminate the tackiness in the area to cause that area to become the tackless area, for example, overcoating with a varnish, a curing agent or other substance or material. In other words, the related approaches employ an additional material of some sort that can be applied in a pattern, like by pattern printing, and will (in some manner) react with or cover the PSA in a selected area so as to convert that area into a tackless area and thereby define a pattern made up of the remaining undetackified or deactivated (i.e. unmodified) adhesive.

In a simpler case, although it is more expensive because it involves another component, separate physical "guard" component(s) (of any type including paper, polymer sheet material or other material) shaped like (parts or the whole of) the desired tackless area can be applied to a preselected area of the cover material such that it is non-removably affixed to the cover material by adhesive on the cover material and thereby becomes the tackless area.

Having described the cover material component of the packaging, now the backing material component will briefly be discussed.

In the simplest case, the backing material is sized and shaped so as to correspond to the size and shape of the cover material when the package is formed. In other words, if single unit packages will be created, the backing will also be single units sized to correspond to their cover material counterpart (for example, the single unit of FIG. 4). Similarly, if a linear array of cover materials (for example, the array of FIG. 5) will be used to create the package, a corresponding linear array of backing material will be used Likewise, if a 2-dimensional array of cover materials (for example, the array of FIG. 6) will be used to create the package, a corresponding array of backing material will be used. Of course, more complicated mix and match configurations of single units and different configuration arrays can be constructed and all are considered to be within the scope herein.

The backing material is processed to create a release island on the backing material sized and shaped so that when the affixation adhesive on the skin side of the dressing contacts the release island it will neither adhere to the release island nor will it materially affect the affixation adhesive's ability to later adhere the dressing to skin. As noted previously, the release island can be a separate conventional release liner which incorporates known release coating technology using appropriate silicone or fluorochemical compound(s), for example as described in U.S. Pat. No. 4,472,480 (incorporated in its entirety herein by reference) and is permanently bonded to the backing material. Alternatively, a portion of the backing material itself, corresponding to at least the perimeter of the dressing which will be packaged between that backing material and the cover material, can be treated so that the portion becomes the release island and functions, in known manner, as the release liner with respect to the dressing but leaves the remainder of the backing that will be part of the package able to adhere to the cover via the adhesive pattern on the cover. Note, that any appropriate known method for creation of the release island can be employed. Accordingly, since there are many ways of doing so and none are essential per se to understanding the packaging approach described herein, the details of doing so need not be elaborated on herein.

The release island is sized and shaped so as to at least substantially conform to the size and shape of the dressing and at least encompasses the area where the affixation adhesive containing side of the dressing will be placed. While it would be possible to use a release island identically corresponding in size and shape to the dressing with which it will be used, as a practical matter it is understood that having a release island that is slightly larger than the periphery allows for slight deviations/imperfections in placement of the dressing.

Alternatively, in some variants where a physically separate release island component is used, the release island can be abutted against the affixation adhesive side of the dressing prior to bonding to the backing material such that placement of the dressing and the release island component will occur concurrently, thereby ensuring proper placement of one relative to the other and relative to the cover material and backing material combination.

Figure 13:
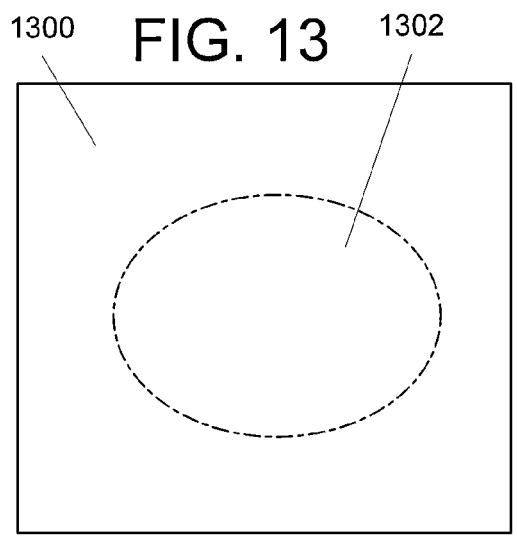
FIG. 13 and FIG. 14 illustrate, in simplified form, representative, non-limiting examples of backing materials which could be used with the cover materials of FIGS. 10 and 11.
Figure 14:
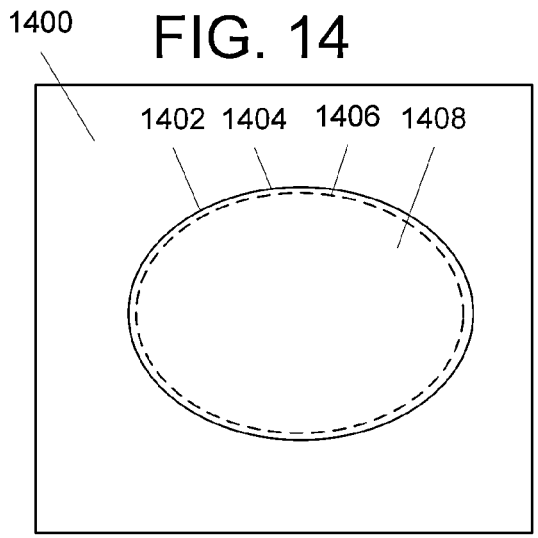

FIG. 13 and FIG. 14 illustrate, in simplified form, representative, non-limiting examples of backing materials 1300, 1400 which could be used with the cover materials of FIGS. 10 and 11. Each respectively has a release island 1302, 1402 thereon, in this instance, intended for use with an oval dressing. In FIG. 13, the release island 1302 is simply a treated area of the backing material 1300 itself, whereas, in contrast, in FIG. 14, the release island is a separate component 1402 whose perimeter 1404 is slightly larger than the perimeter 1406 of the intended dressing 1408.

Figure 12:
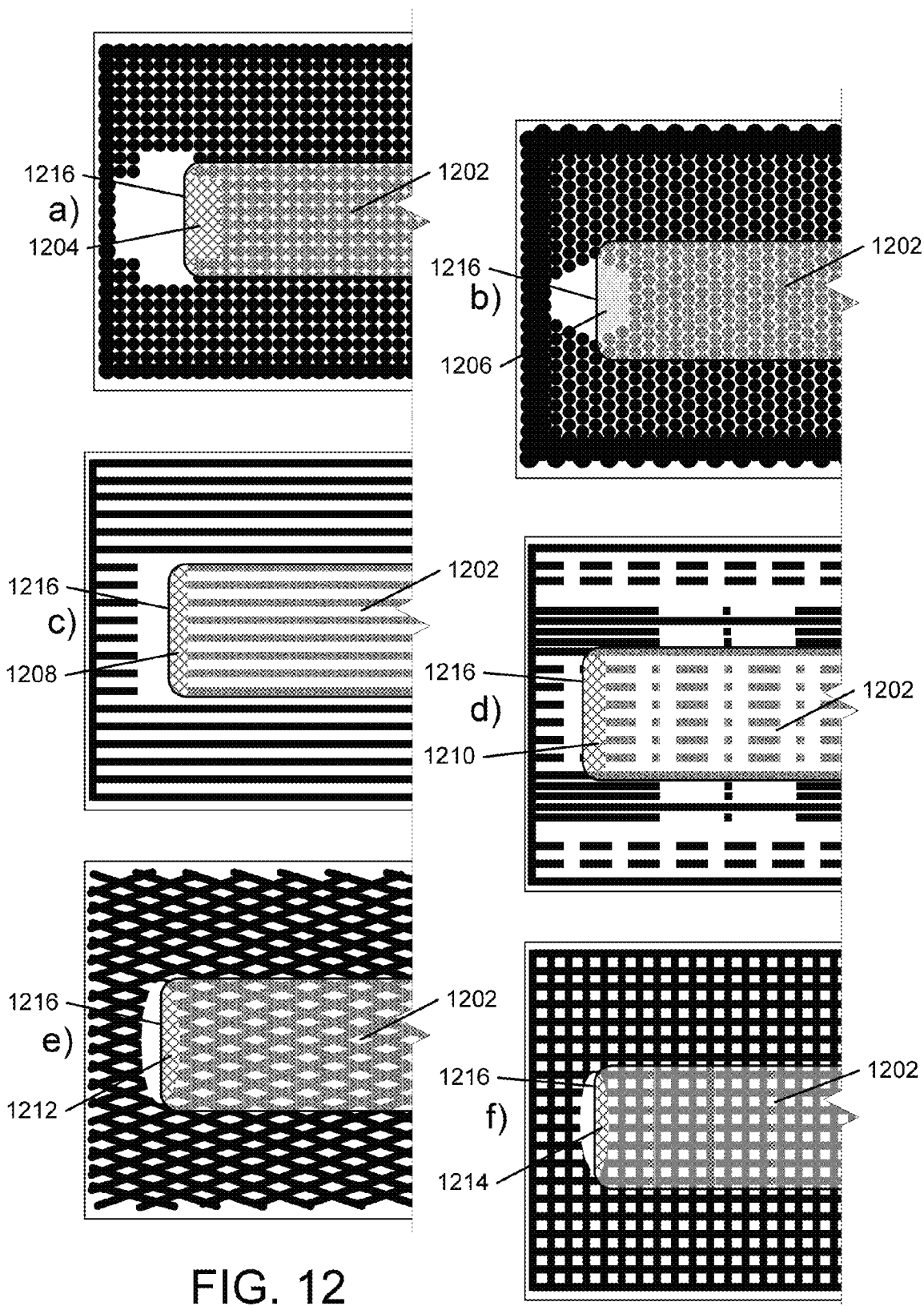
FIGS. 12a through 12f, are similar to FIGS. 11a through 11f, except that FIGS. 12a through 12f illustrate portions of the cover materials of FIG. 11 and the outline of a rectangular dressing.
Figure 15:
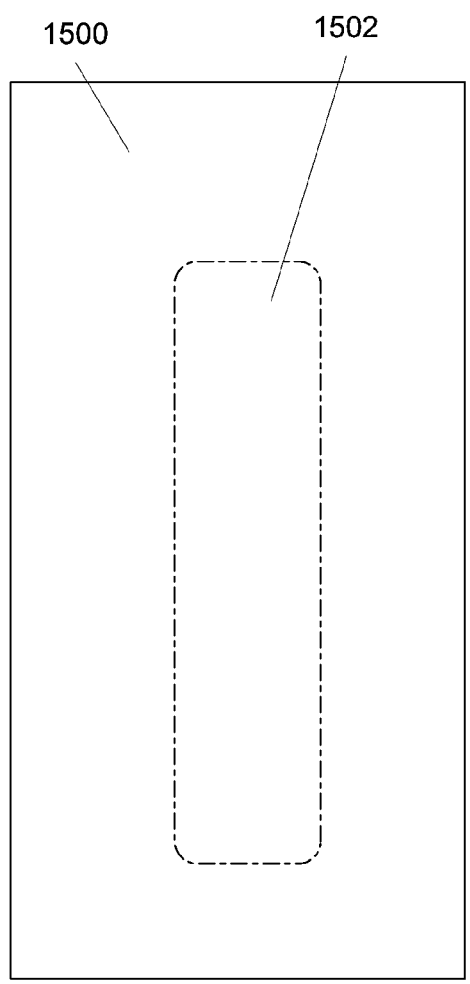
FIG. 15 and FIG. 16 illustrate, in simplified form, representative, non-limiting examples of backing materials which could be used with the cover materials of FIG. 12.
Figure 16:
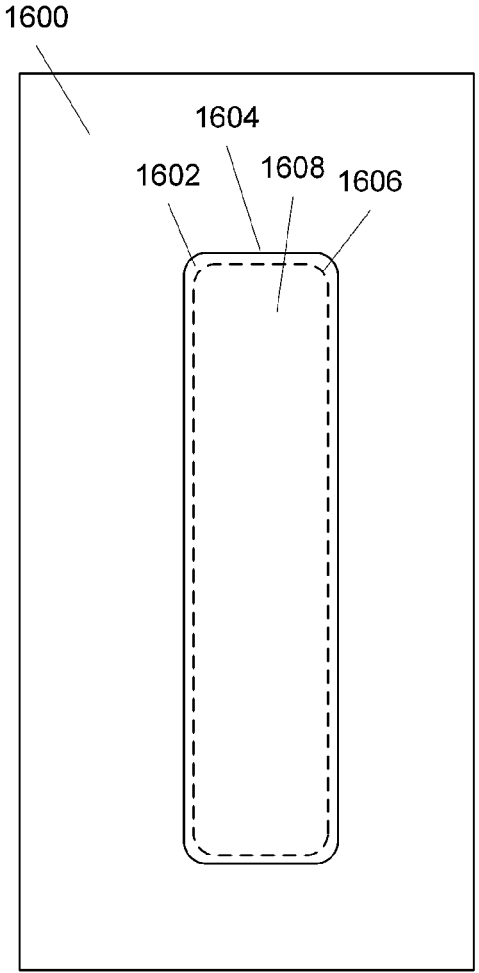

FIG. 15 and FIG. 16 illustrate, in simplified form, representative, non-limiting examples of backing materials 1500, 1600 which could be used with the cover materials of FIG. 12. Again, each respectively has a release island 1502, 1602 thereon, in this instance, intended for use with a common elongated rectangular dressing. Like in FIG. 13, the backing material 1500 of FIG. 15, has a release island 1502 that is simply a treated area of the backing material 1500 itself. In contrast, in FIG. 16, the release island is a separate component 1602 whose perimeter 1604 is slightly larger than the perimeter 1606 of the intended dressing 1608.

At this point, it should be noted that, for some variants, creation of the cover material with its patterned adhesive could occur entirely before creation of the backing material with its release island, where as for other variants, the backing material can be created entirely before the cover material, and with still other variants, creation of the cover material and backing material could occur partially or entirely concurrently.

Now, once both the cover material and backing material have been completely created, creation of the final package is straightforward. The dressing is located between the side of the cover material containing the pattern of adhesive and the side of the backing material containing the release island (as shown in exploded views in FIGS. 2 and 3) positioned such that one terminus of the dressing overlies the tackless area in the manner described above and the peripheral perimeter orientation of the dressing substantially corresponds to the release island perimeter. The cover material and backing material are brought together such that the part of the pattern of adhesive on the cover material corresponding to the dressing will adhere to the dressing as described above, and the remainder will removably attach the cover material and backing material together such that the high tack PSA between the cover material and backing material will form a seal, of closed shape, encompassing the entire periphery of both the dressing and the tackless area, thereby forming a hermetic seal about the dressing and the tackless area.

Figure 17:
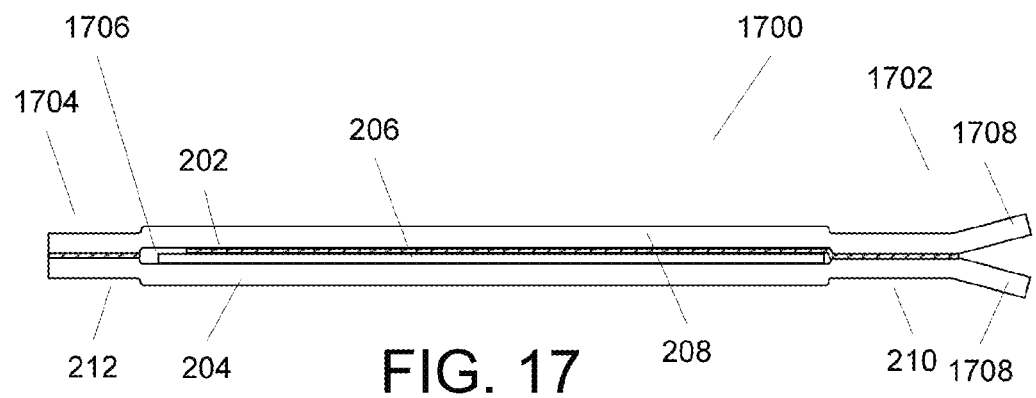
FIG. 17 illustrates, in simplified form, a side view cross section of a package 1700 constructed using one variant of the process herein.

FIG. 17 illustrates, in simplified form, a side view cross section of a package 1700 constructed using one variant of the process herein. Although not previously described, the end 1702 of the package 1700 opposite the end 1704 with the tackless area 1706 will also include some configuration to assist in opening the packages. Depending upon the particular variant, the configuration can range from the formation of a pair of flaps 1708 by bending the extreme end of both the cover material and backing material at the opening end away from each other, such as shown in FIG. 17, or back on themselves in a conventional manner, or using any other conventional method to facilitate opening via the opening end.

Figure 18:
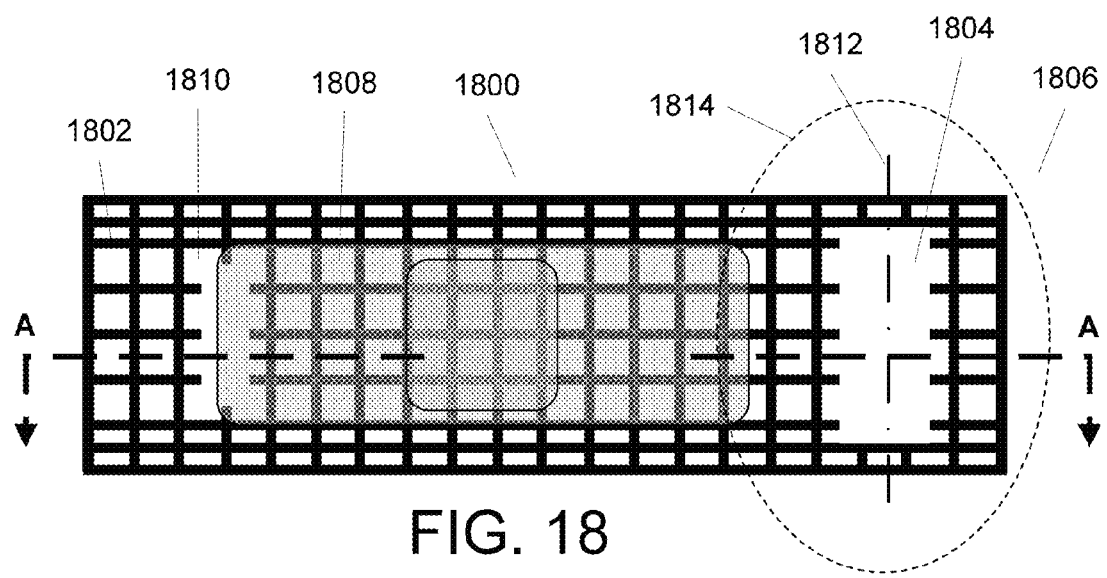
FIG. 18, illustrates, in simplified form, an example cover material suitable for an optional alternative variant of the approach herein.
Figure 19:
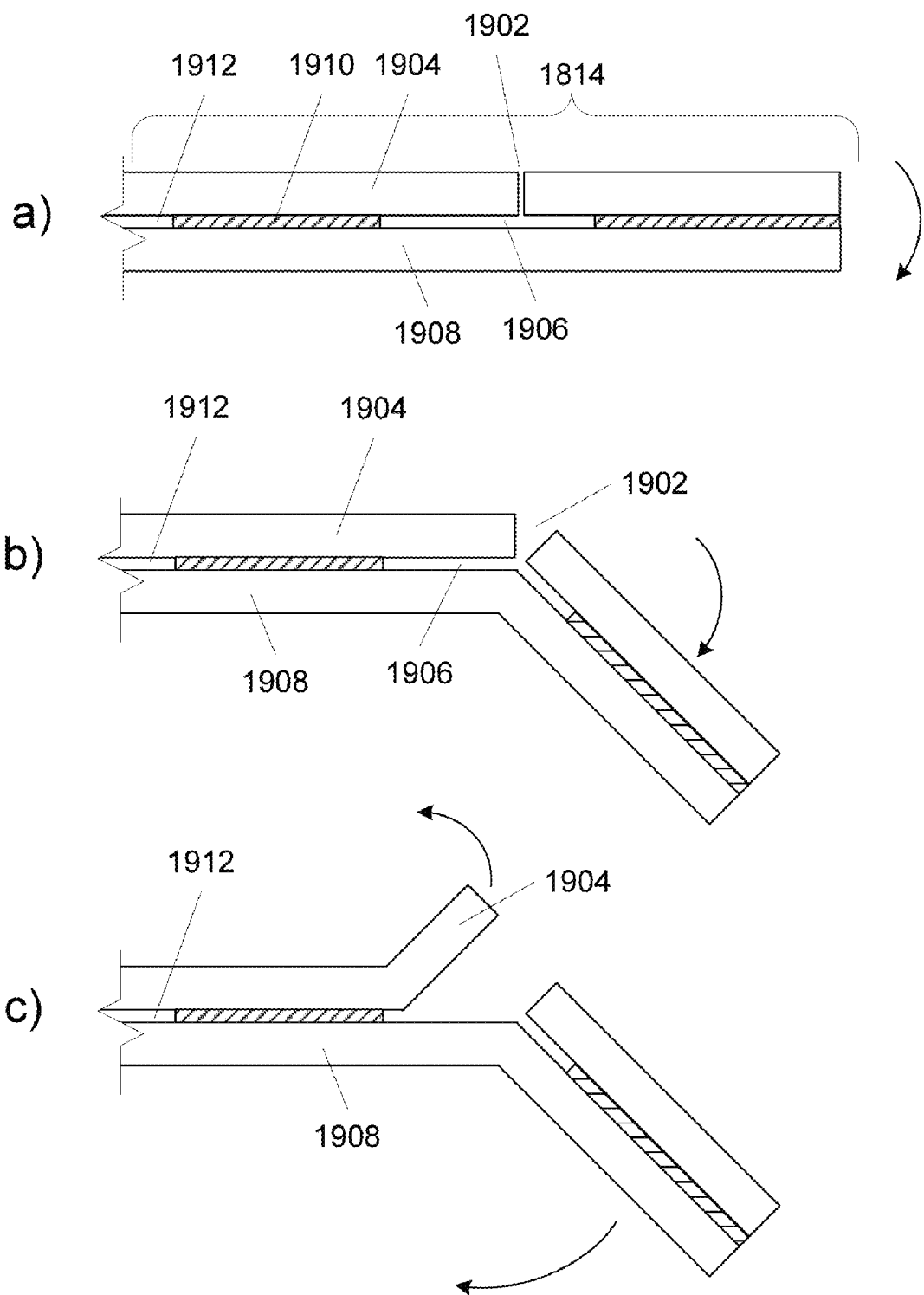
FIGS. 19a through 19c respectively illustrate, in highly enlarged (but not to scale) simplified form, a cross section of a portion of the cover of FIG. 18 when part of a package.
Figure 20:
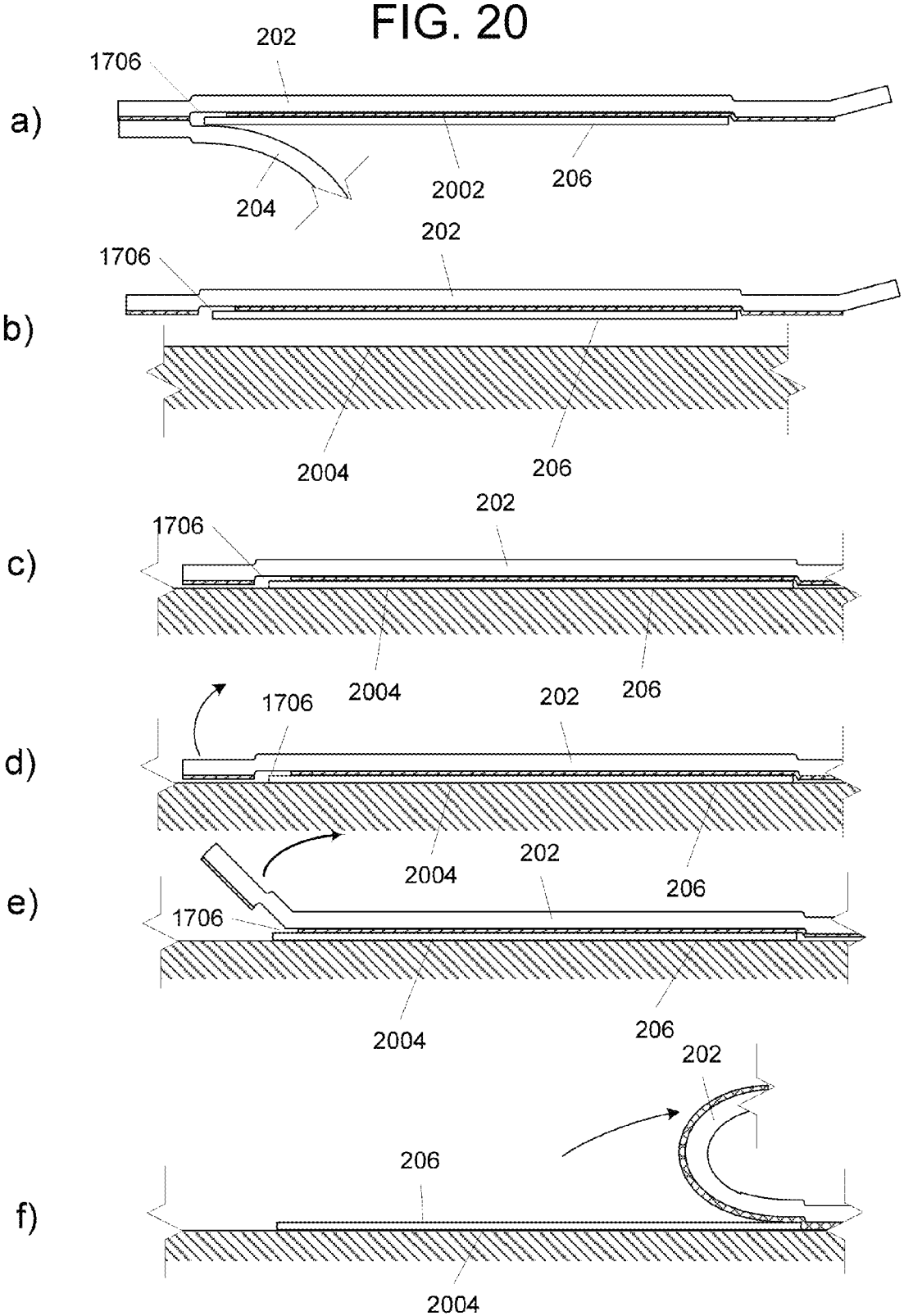
FIG. 20a through 20f illustrate, in simplified form, the use of the package of FIG. 17.

Alternatively, and advantageously, a further optional variant of the approach can be used to facilitate opening. FIG. 18, illustrates, in simplified form, an example cover material 1800 having a predetermined pattern of lines 1802 of high tack PSA suitable for such a variant approach. With this variant approach, a secondary tackless area 1804 is formed on the cover material near the opening end 1806 and wholly outside the closed shape of adhesive forming the hermetic seal about the dressing 1808 and tackless area 1810 described above. This secondary tackless area 1804 is positioned such that after the package is formed as described above, one of the cover material or backing material can be cut or scored following a line 1812 passing through the secondary tackless area 1804. In this manner, the secondary tackless area 1804 can be used to facilitate opening of the package after creation. This will be shown for a portion 1814 of this cover as used in a package involving a cross section taken along A-A.

FIGS. 19a through 19c respectively illustrate, in highly enlarged (but not to scale) simplified form, a cross section of the portion 1814 of the cover of FIG. 18 taken along A-A when part of a package 1900. As shown in FIG. 19a, in this example, a score or cut 1902 has been made entirely through one of the materials 1904 (cover or backing) over the tackless area 1906 while leaving the other material 1908 of the package 1900 intact and without disturbing the adhesive 1910 that is part of the closed shape of adhesive which forms the hermetic seal for the dressing 1912 (only a small part of the terminus near the opening end being visible). By flexing the material 1908 away from the score or cut 1902 (FIG. 19b), the tackless area 1906 allows the part of the materials 1904, 1908 sandwiching the dressing to be separated from each other (by motion of removing the cover material/dressing combination from the backing, removing the backing from the cover material/dressing combination, or by splitting the two from each other by pulling equally on both material parts 1904, 1908) (FIG. 19c) to open the package 1900.

Thus, one major variant of the package creation process can be summed up as follows:

In one sub-operation, the surface of a cover material which will contact the back side of a dressing is coated, in a predetermined pattern, with a detachable high tack, pressure sensitive adhesive. The pattern of PSA is such that:
  (i) the surface of the cover material includes at least one tackless area. The tackless area is devoid of adhesive and disposed to correspond to and encompass at least a substantial portion of an edge of the terminus of a dressing that is farthest from the intended opening end of the package as well as a portion of the surface of the cover material just beyond the edge of first terminus (in the direction away from the opening end);
  (ii) the high tack, PSA forms at least a closed shape that encompasses within it both the tackless area and a dressing receiving area; and
  (iii) the high tack, PSA is disposed to affix the back side of the dressing to the surface of the cover material along the extent of the dressing (except the tackless area) when the back side of the dressing contacts the high tack, PSA on the surface of the cover material.

In another sub-operation, a release island is formed on one surface of a backing material, with the release island having a size and shape corresponding to the width, extent and perimeter of the dressing.

The sub-operation involving patterning adhesive on the cover material and the sub-operation involving creation of the release island on the backing can occur in any order or overlap in time, in whole or part.

In an additional sub-operation, a dressing is sandwiched between the adhesive-containing first surface of the cover material and the first surface of the backing material. The dressing placement is such that:
  (i) the skin adhering side of the dressing will be in contact with and substantially correspond to the release island;
  (ii) substantially all of the extent of the back side of the dressing will be in contact with, and held by, the high tack, PSA on the surface of the cover material;
  (iii) a substantial portion of the edge of the terminus of the dressing farthest from the intended opening end of the package overlays the tackless area and, thereby defines an application end for the dressing; and
  (iv) the closed shape of high tack, pressure sensitive adhesive forms a hermetic seal about the dressing, with the hermetic seal encompassing at least the entire perimeter of the dressing and the tackless area on the first surface of the cover material.

An alternative major variant of the package creation process can similarly be summed up as follows:

In one sub-operation at least a portion of a surface of a cover material is coated with a detachable high tack, PSA. Then, the tack of at least one predetermined area of the detachable high tack, PSA is modified in a predetermined pattern so that the at least one predetermined area becomes a tackless area bounded by unmodified high tack, PA. The unmodified high tack, PSA will include a dressing receiving area that is located (i) so as to correspond to and encompass at least a substantial portion of an edge of the terminus of the dressing that is farthest from the intended opening end of the package and at least a portion of the surface of the cover material just beyond the edge of the terminus, and (ii) such that the unmodified high tack, PSA will be disposed to affix the back side of the dressing to the surface of the cover material along the most of the extent of the dressing when the back side of the dressing is brought into contact with the unmodified high tack, pressure sensitive adhesive on the surface of the cover material in the dressing receiving area.

In another sub-operation, a release island is formed on a surface of a backing material, with the release island having a size and shape corresponding to at least the width, extent and perimeter of the dressing.

Again the immediately preceding two sub operations can occur in any order or overlap in time, in whole or part.

In a further sub operation, the dressing is sandwiched between the surface of the cover material and the surface of the backing material such that: (i) the skin adhering side of the dressing will be in contact with and substantially correspond to the release island; (ii) substantially all of the extent of the back side of the dressing will be in contact with, and held by, the unmodified high tack, PSA located in the dressing receiving area of the cover material; (iii) a substantial portion of the edge of the terminus of the dressing farthest from the opening end overlays the tackless area; and (iv) the unmodified high tack, PSA will form a hermetic seal encompassing at least the entire perimeter of the dressing and the tackless area.

Figure 21:
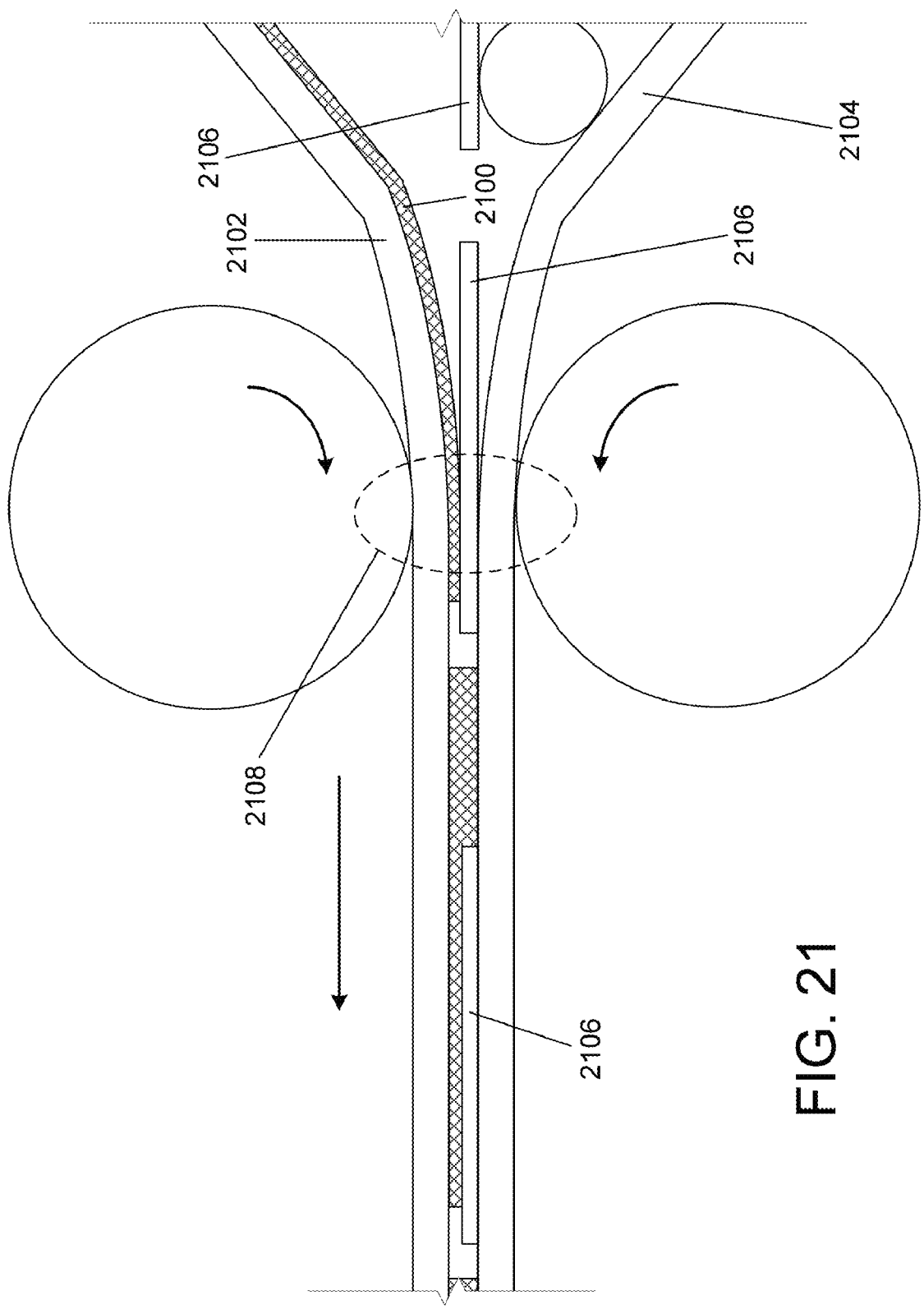
FIG. 21 illustrates, a simplified representative example of a progressive package formation sub-variant approach.

Note that, with both of the foregoing major variants, the sandwiching sub-operation can involve different sub variants, for example, one sub variant could involve bringing the dressing into contact with the PSA on the cover before the cover and backing are brought together. Another sub-variant could involve placing the dressing on the release island before the cover and backing are brought together. Yet another sub-variant could have the cover, dressing and backing all progressively brought together from one end to the other. FIG. 21 illustrates, a simplified representative example of this progressive package formation sub-variant approach in which the patterned adhesive 2100 and cover material 2102 combination are fed in known manner from one source (not shown). the backing material 2104 is fed in known manner from another source (not shown) and the individual dressings 2106 are sequentially fed in known manner from a third source (not shown) so they are all brought into contact with each other at essentially the same time in substantially the same location 2108.

An advantageous byproduct of the variants described herein is that the created package makes application of the dressing to the skin easier. This is shown in the sequence of FIG. 20*a* through 20*f* which illustrates, in simplified form, the use of the package of FIG. 17 (i.e. an example package constructed according to one variant of the process described herein).

Specifically, FIG. 20*a* illustrates the package 1700 after the backing material 204 has been peeled away along most of the entire extent of the dressing 206. Note that the dressing 206 continues to be adhered to, and supported by the cover material 202 by the pattern of adhesive 2002 on the cover material 202.

FIG. 20*b* illustrates the cover material 202 and dressing 206 combination after the backing material 204 has been fully removed and is placed just above a skin surface 2004. At this point it is worth noting that a further advantageous byproduct of some of the variants described herein is that curling or arching of the cover material 202 end(s) in a direction away from the dressing 206 can be avoided or minimized so as to be negligible.

FIG. 20*c* illustrates the cover material 202 and dressing 206 combination as the affixation adhesive on the skin side of the dressing 206 is brought into contact with the skin surface 2004.

FIG. 20*d* illustrates the cover material 202 and dressing 206 combination following the affixation adhesive on the skin side of the dressing 206 affixing the dressing 206 to skin surface 2004 and immediately prior to removal of the cover material 202. To effect the removal of the cover material 202, the end containing the tackless area 1706 is lifted as shown in FIG. 20*e*. Advantageously, because the tackless area 1706 underlies a portion of the terminus of the dressing 206, it is easy to release the dressing 206 from the cover material 202 via this end because the tackless area 1706, in effect, "breaks the seal" formed by the pattern of adhesive holding the dressing 206 to the cover material 202, thereby, as shown in FIG. 20*f*, allowing it to be peeled back off the dressing 206 with substantially less force than would be required to dislodge the dressing 206 from the skin and allow the dressing 206 to remain in place.

Figure 22:
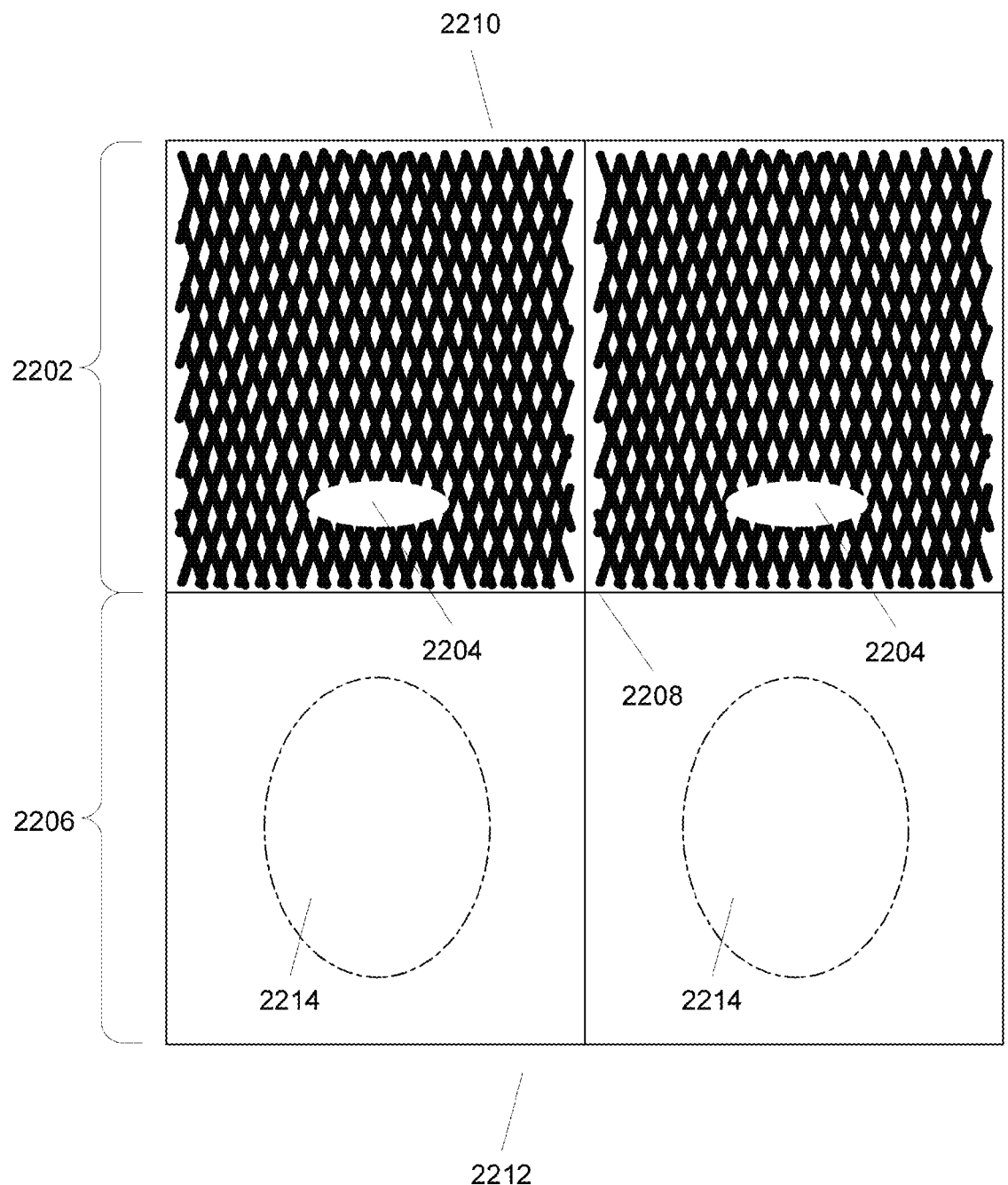
FIG. 22 illustrates, in simplified example form, a sub variant processed as described herein for construction of a unified package configuration.

On a related note, with some variants, the cover material 202 and backing material 204 could be the same material and, in some cases, be part of the same sheet (i.e. have "unified" package components). FIG. 22 illustrates, in simplified example form, a sub variant processed as described herein for construction of a unified package configuration. With such variants one portion 2202 would be treated as the cover material and patterned with the adhesive and have a tackless portion 2204 as described herein, with the tackless portion placed closest to the portion 2206 which will serve as the corresponding backing material. The portion 2206 which would serve as the backing material would be treated, or have a component attached to it, to form the release island 2214 as described herein. A package would then be created by folding about the line 2208 between the cover portion 2204 and the backing portion 2206 with the dressing in between the two portions. Note that, with this configuration the fold line will advantageously most efficiently be located at the application end of the package and the edges 2210, 2212 of the two portions 2202, 2206 farthest from each other will most efficiently be located at the opening end of the package.

Finally, with respect to wound dressings and drug delivery dressings in particular, and likely other dressings as well, it will be desirable to sterilize the package (or its components individually), either before a sterile dressing is inserted or after the completed package is formed. This aspect is irrelevant to understanding the invention or the various implementation variants and can be performed by any known process that does not preclude the package from being created as described herein or, if already created, destroy its ability to perform as intended. As a result, in some cases, the sterilization approach will be limited by the make up of the items used to create the package or, the items used to create the package will be influenced by the intended sterilization method. The ability to handle the interrelationship of material selection and sterilization is well within the knowledge of those of ordinary skill in the art, so it is not discussed herein. In fact, it is possible that the sterilization process could, in some variants, be part of the process of forming a tackless area, for example, if it involves application of light outside the visible spectrum, application of heat, exposure to a particular fluid, etc.

Materials

Having now described the process, for purposes of understanding, a brief explanation of materials that can be involved in the process will now be described.

Depending upon the particular intended configuration, different materials can be used in the process described herein as the various components. In this regard, it should be understood that the particular materials may depend, for example, on the particular dressing to be packaged, whether, and to what extent, the cover material or backing material may contain printing, whether there is a need or desire for either or both of the cover material or backing material to be transparent, translucent or opaque in whole or part, the specific package adhesive to be used, etc. Thus, the mention of any particular materials below are intended to be exemplary and neither limiting nor exhaustive.

A representative example material suitable for use as the cover material is removable clear polypropylene No. FP0862, commercially available from 3M, 1030 Lake Road, Medina, Ohio 44256-0428. However, any commercially available material which is adhesive-compatible and sufficiently stiff enough to resist curling or arching of the dressing when the cover material and dressing are adhered together will work.

A representative example material suitable for use as the backing material is uncoated, 32 lb, 25% cotton fine finish paper, commercially available from numerous sources. However, any material which can incorporate a release island as described herein and which is adhesive compatible such that, in combination with the cover material and adhesive, it can form a hermetic seal about a dressing can be used. Where a separate release liner is used as the release island, Uline 40 lb super calendared bleached kraft paper treated with an appropriate silicone or fluorochemical compound, or other known release liner material can be used.

Suitable removable high tack, pressure sensitive adhesives for film or paper include, by way of non-limiting example, Fasson® brand R3500 PSA, commercially available from the Fasson division of Avery Dennison Corp., Miller Corporate Center, 150 North Orange Grove Boulevard, Pasadena, Calif. 91103. Again, any other removable high tack, pressure sensitive adhesive from this same source, or any other source, that is compatible with the selected cover material and backing material can be used.

To ensure completeness and provide ancillary details relating to dressings, release island/release liner creation, available cover materials per se, available backing materials per se, and dressing packaging in general, the entire disclosures of each of the following U.S. Patents and U.S. Published Patent Applications are incorporated herein by reference in their entirety as if fully set forth herein: U.S. Pat. Nos. 8,084,665, 8,021,347, 7,858,838, 7,521,586, 7,518,031, 6,905,100, 6,878,385, 6,838,589, 6,822,132, 6,706,940, 6,573,421, 6,495,230, 6,350,339, 6,297,422, 6,225,522, 6,184,264, 6,149,614, 6,124,522, 6,008,429, 5,998,694, 5,951,505, 5,755,681, 5,738,642, 5,726,250, 5,685,833, 5,511,689, 5,423,737, 5,415,627, 5,412,035, 5,397,297, 5,336,162, 5,160,315, 5,106,629, 5,018,516, 4,915,228, 4,832,008, 4,706,662, 4,513,739, 4,472,480, 2011/0257574, 2011/0166492, 2010/0222731, 2009/0187130, 2009/0082710, 2008/0281246.

It should be understood that this description (including the figures) only includes some illustrative embodiments. For the convenience of the reader, the illustrative embodiments of the above description is a representative sample of all possible embodiments, a sample that teaches the principles of the invention. The description has not attempted to exhaustively enumerate all possible variations. That alternate embodiments may not have been presented for a specific portion of any variant, or that further non-described alternate embodiments may be available for a portion of a variant, is not to be considered a disclaimer (intentional or unintentional) of those alternate embodiments. One of ordinary skill will appreciate that many of those non-described embodiments incorporate the same principles of the claimed invention and that others are equivalent thereto.

What is claimed is:

1. A method of making a packaged dressing, the dressing having a width, an extent and a perimeter, the dressing comprising a skin adhering side having an affixation adhesive thereon, and a back side opposite the skin adhering side, the dressing further comprising a first terminus at one end of the extent and a second terminus at the other end of the extent, the second terminus defining an opening end for the packaged dressing, the method comprising:
   A) coating at least a portion of a first surface of a cover material with a detachable high tack, pressure sensitive adhesive;
   B) modifying the tack of at least one predetermined area of the detachable high tack, pressure sensitive adhesive in a predetermined pattern so that the at least one predetermined area becomes a tackless area bounded by unmodified high tack, pressure sensitive adhesive, and such that, following the modifying, the high tack, the pressure sensitive adhesive that was not subject to the modifying will be unmodified high tack, pressure sensitive adhesive and will include a dressing receiving area, the predetermined area being located
      (i) so as to correspond to and encompass at least a substantial portion of an edge of the first terminus and at least a portion of the surface of the cover material just beyond the edge of the first terminus,
      (ii) such that the unmodified high tack, pressure sensitive adhesive will be disposed to affix the back side of the dressing to the first surface of the cover material along most of the extent of the dressing when the back side of the dressing is brought into contact with the unmodified high tack, pressure sensitive adhesive on the first surface of the cover material in the dressing receiving area,
   C) forming a release island, on a first surface of a backing material, having a size and shape corresponding to at least the width, extent and perimeter of the dressing;
   D) sandwiching the dressing between the first surface of the cover material and the first surface of the backing material such that
      (i) the skin adhering side of the dressing will be in contact with and substantially correspond to the release island,
      (ii) substantially all of the extent of the back side of the dressing will be in contact with, and held by, the unmodified high tack, pressure sensitive adhesive in the dressing receiving area on the first surface of the cover material,
      (iii) a substantial portion of the edge of the first terminus of the back side of the dressing overlays the tackless area, and
      (iv) the unmodified high tack, pressure sensitive adhesive will form a hermetic seal encompassing at least the entire perimeter of the dressing and the tackless area.

2. The method of claim 1, wherein the modifying the tack of at least one predetermined area comprises:
   detackifying the high tack, pressure sensitive adhesive within the predetermined area.

3. The method of claim 2, wherein the detackifying includes:
   pattern printing a substance onto the high tack, pressure sensitive adhesive.

4. The method of claim 3, wherein the substance includes at least one of:
   a varnish or a solvent.

5. The method of claim 2, wherein the detackifying includes:
   applying material onto the high tack, pressure sensitive adhesive in at least one pre-specified area.

6. The method of claim 2, wherein stickiness of the high tack, pressure sensitive adhesive can be substantially eliminated by exposure to light outside the visible light spectrum, and wherein the deactivating includes:
   exposing a portion of the high tack, pressure sensitive adhesive to the light outside the visible light spectrum in a pre-specified pattern.

7. The method of claim 6, wherein the light outside the visible spectrum includes ultraviolet light.

8. The method of claim 1, wherein the modifying the tack of at least one predetermined area comprises:
   deactivating the high tack, pressure sensitive adhesive within the predetermined area.

9. The method of claim 1, wherein the tackless area defines a pattern of lines of adhesive.

10. The method of claim 9, wherein at least two lines of the pattern of lines intersect.

11. The method of claim 9, wherein at least three lines of the pattern of lines are evenly spaced.

12. The method of claim 1, wherein the tackless area defines a pattern of dots of adhesive.

13. The method of claim 1, wherein the tackless area defines a predetermined pattern of adhesive.

14. The method of claim 1, wherein the modifying the tack of at least one predetermined area comprises:
over-coating the high tack, pressure sensitive adhesive within the predetermined area.

15. The method of claim 14, wherein the over-coating comprises:
applying a varnish onto the high tack, pressure sensitive adhesive in a pre-specified pattern.

16. The method of claim 1, further comprising:
forming a second tackless area between the cover material and the backing material outside the hermetic seal near the second terminus end.

17. The method of claim 16, further comprising:
scoring a line into one of the cover material or the backing material passing through the second tackless area.

* * * * *